(12) United States Patent
Wang et al.

(10) Patent No.: US 8,003,358 B2
(45) Date of Patent: *Aug. 23, 2011

(54) TWO-STEP ENZYME METHOD FOR PREPARING 7-AMINOCEPHALOSPORANIC ACID

(75) Inventors: Jun Wang, Fo Tan (HK); Waikei Tsang, Tai Po (HK); Hongkin Yap, Tai Po (HK); Junmin Chen, Shenzhen (CN); Yaulung Siu, Kowloon (HK); Supyin Tsang, Kowloon (HK)

(73) Assignee: Bioright Worldwide Company Limited, Tortola (GB)

( * ) Notice: Subject to any disclaimer, the term of this patent is extended or adjusted under 35 U.S.C. 154(b) by 617 days.

This patent is subject to a terminal disclaimer.

(21) Appl. No.: 11/990,115

(22) PCT Filed: Aug. 2, 2006

(86) PCT No.: PCT/CN2006/001940
§ 371 (c)(1),
(2), (4) Date: Apr. 29, 2008

(87) PCT Pub. No.: WO2007/016861
PCT Pub. Date: Feb. 15, 2007

(65) Prior Publication Data
US 2010/0112633 A1    May 6, 2010

(30) Foreign Application Priority Data
Aug. 8, 2005   (CN) .......................... 2005 1 0089965

(51) Int. Cl.
| | |
|---|---|
| C12N 9/02 | (2006.01) |
| C12N 9/10 | (2006.01) |
| C12N 1/20 | (2006.01) |
| C12N 15/00 | (2006.01) |
| C12Q 1/00 | (2006.01) |
| C12Q 1/26 | (2006.01) |
| C07H 21/04 | (2006.01) |
| C12P 17/18 | (2006.01) |

(52) U.S. Cl. .............. 435/189; 435/4; 435/119; 435/25; 435/69.1; 435/71.1; 435/252.3; 435/320.1; 435/193; 536/23.2

(58) Field of Classification Search ......................... None
See application file for complete search history.

(56) References Cited

U.S. PATENT DOCUMENTS
7,517,677 B2 *  4/2009  Wang et al. ................... 435/190

FOREIGN PATENT DOCUMENTS
| | | |
|---|---|---|
| CN | 1104255 | 6/1995 |
| CN | 1301813 | 7/2001 |
| CN | 1371999 | 10/2002 |
| CN | 1428424 | 7/2003 |

OTHER PUBLICATIONS

Branden et al. Introduction to Protein Structure, Garland Publishing Inc., New York, p. 247, 1991.*
Pollegioni et al. "Cloning, sequencing and expression in *E. coli* of a D-amino acid oxidase cDNA from *Rhodotorula gracilis* active on cephalosporin C" Journal of Biotechnology 58 (1997) pp. 115-123.
Molla et al. "Overexpression in *Escherichia coli* of a Recombinant Chimeric *Rhodotorula gracilis* D-Amino Acid Oxidase" Protein Expression and Purification 14, (1998) pp. 289-294.
Ishiye et al. "Nucleotide sequence and expression in *Escherichia coli* of the *Cephalosporin acylase* gene of a *Pseudomonas strain*" Biochimica et Biophysicia Acta, 1132 (1992) pp. 233-239.

* cited by examiner

*Primary Examiner* — Yong Pak
(74) *Attorney, Agent, or Firm* — McDermott Will & Emery LLP

(57) ABSTRACT

The present invention discloses a two-step enzyme method for preparing 7-aminocephalosporanic acid from cephalosporin C, wherein D-amino acid oxidase used is purified D-amino acid oxidase mutant of yeast *Trigonopsis variabilis*, having a specific activity of 105% higher than that of parent D-amino acid oxidase. The method has no need of addition of hydrogen peroxide, β-lactamase inhibitor, catalase inhibitor, catalase and the like commonly used in the prior art. The productivity of the method can reach more than 93%. Thus, the method is simple, low in cost and high in productivity.

10 Claims, 8 Drawing Sheets

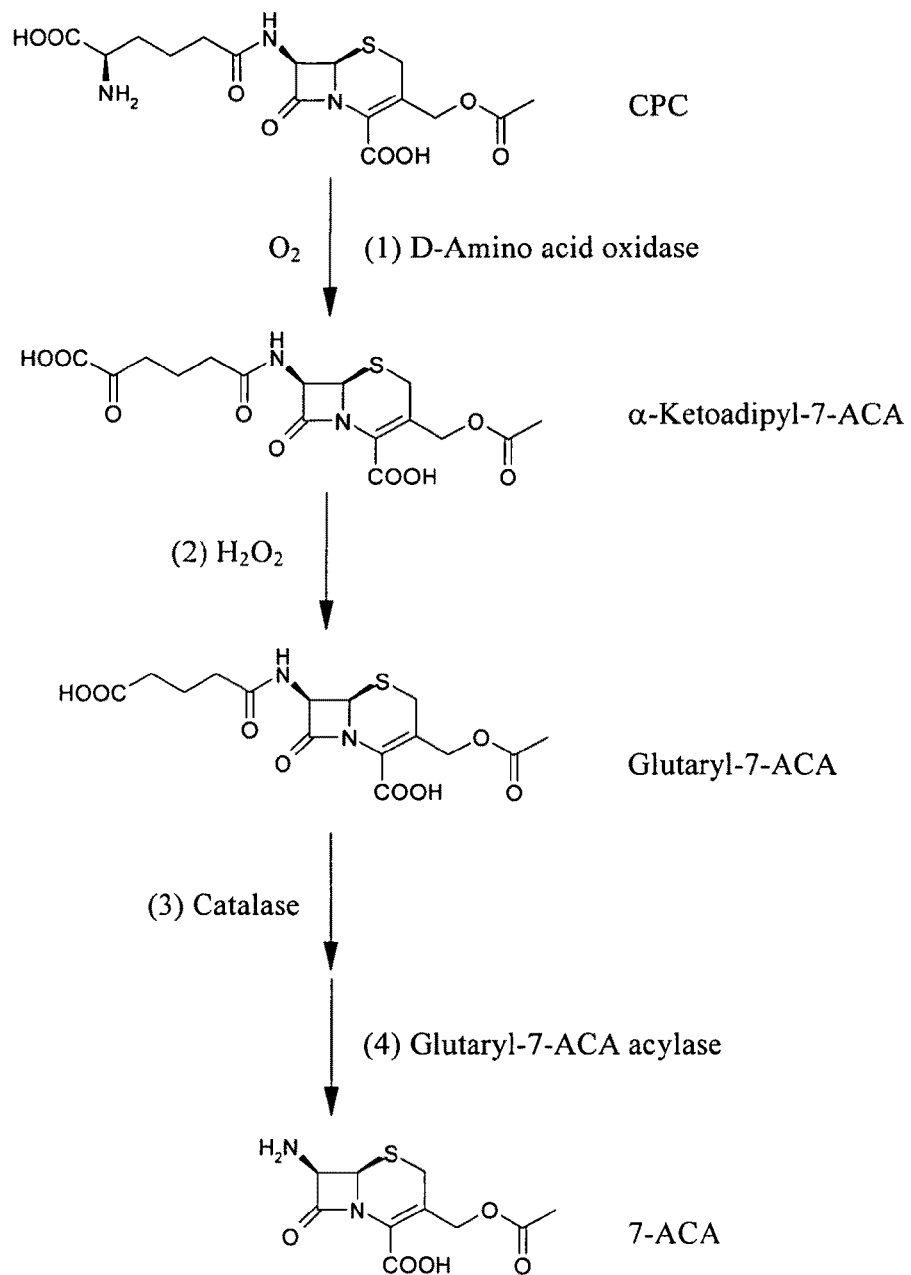
Fig. 1 the reaction flow chart of conventional conversion of CPC to 7-ACA.

Fig. 2 expression vector pHS-GHA.
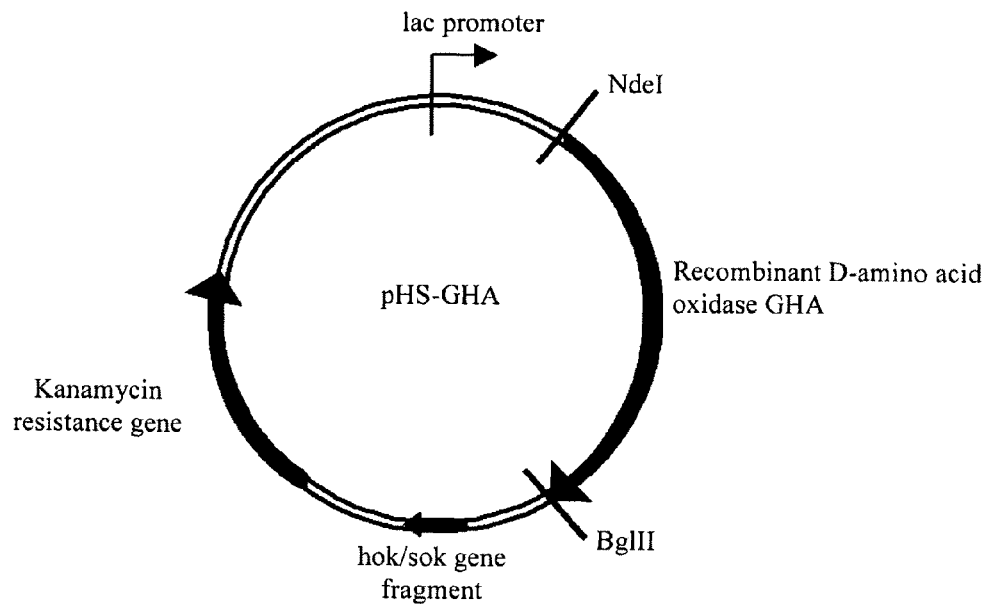
Fig. 3 expression vector pT7-kan-ACY.
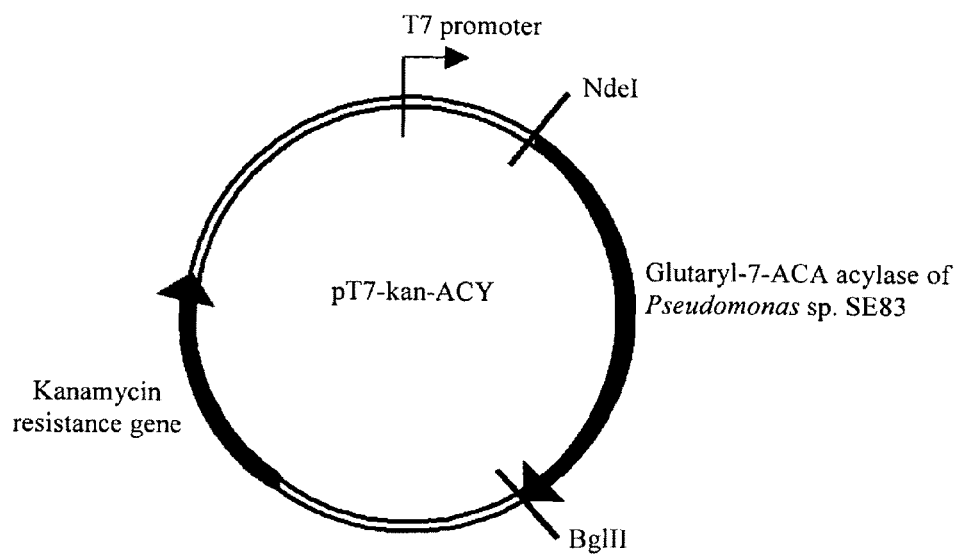

Fig. 4 expression vector pRSET-lac-GI-hok/sok-kan.
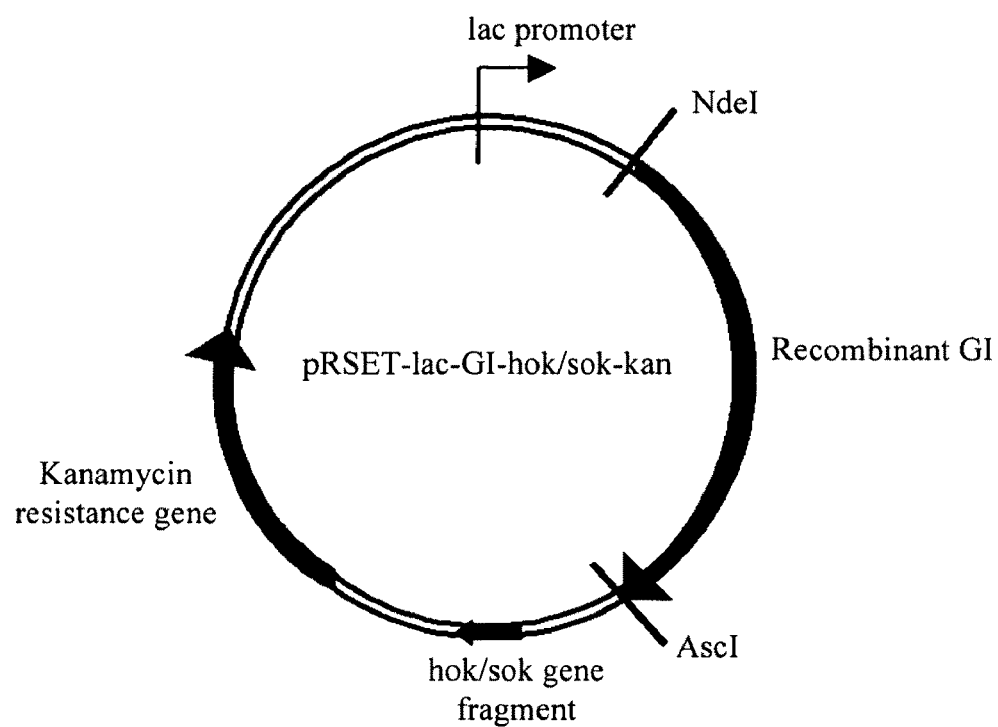

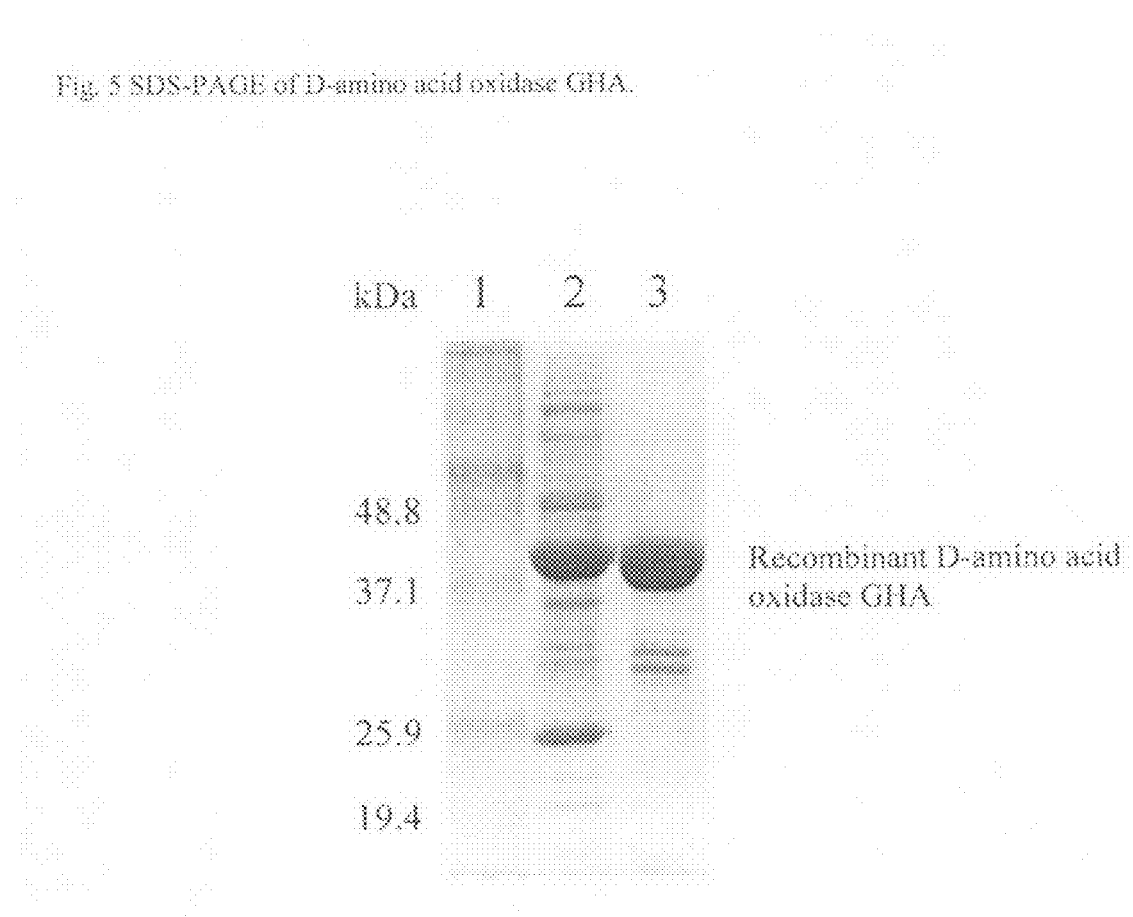
Fig. 5 SDS-PAGE of D-amino acid oxidase GHA.

Fig. 6 the HPLC chromatogram of the conversion of CPC to glutaryl-7-ACA by D-amino acid oxidase GHA.
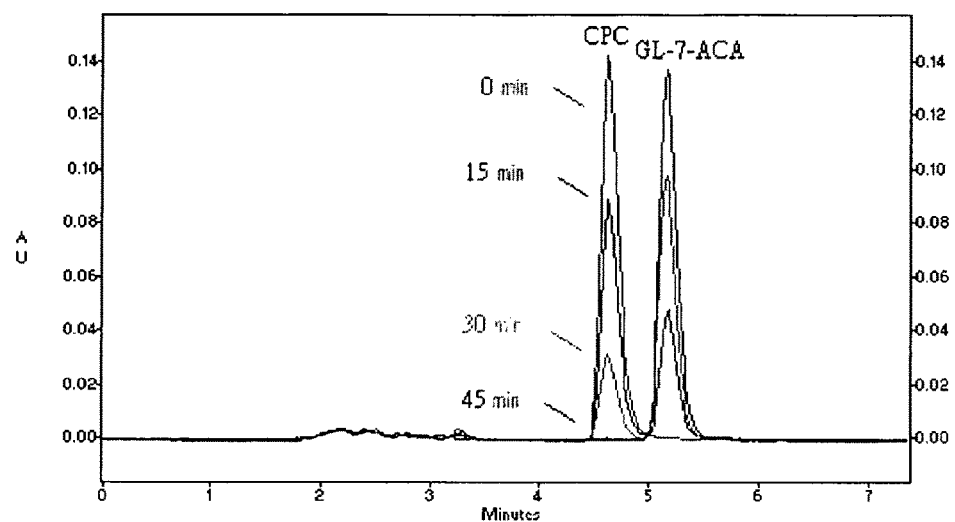

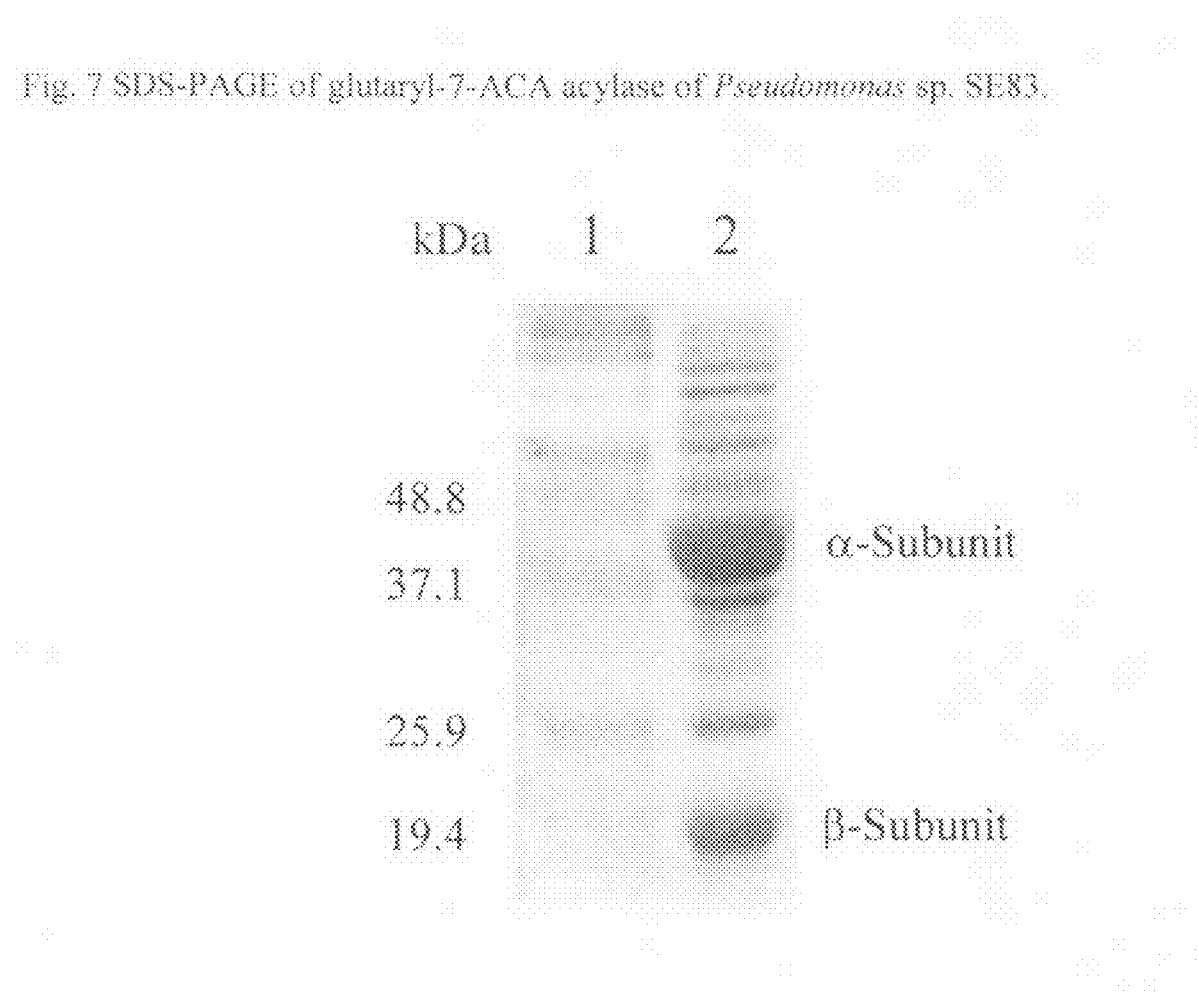
Fig. 7 SDS-PAGE of glutaryl-7-ACA acylase of *Pseudomonas* sp. SE83.

Fig. 8 the HPLC chromatogram of the conversion of glutaryl-7-ACA to 7-ACA by glutaryl-7-ACA acylase of *Pseudomonas* sp. SE83.
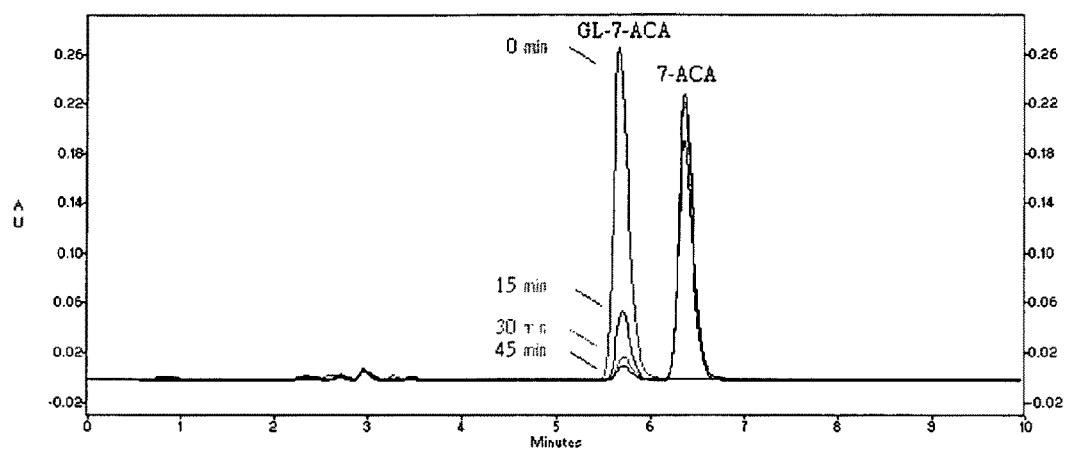

Fig. 9 the HPLC chromatogram of the conversion of CPC to 7-ACA by the two-step enzyme method.
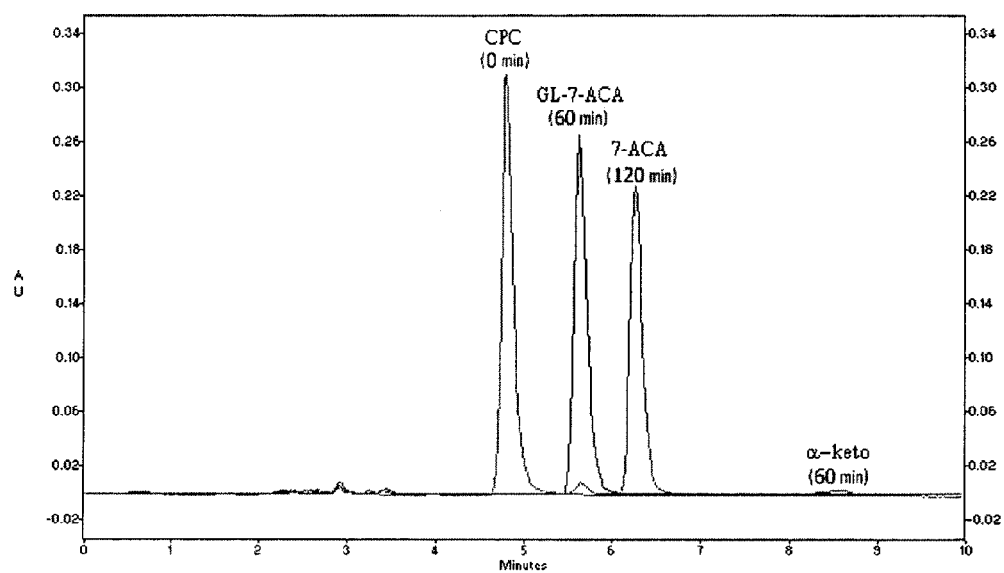

US 8,003,358 B2

TWO-STEP ENZYME METHOD FOR PREPARING 7-AMINOCEPHALOSPORANIC ACID

RELATED APPLICATIONS

This application is the U.S. National Phase under 35 U.S.C. §371 of International Application No. PCT/CN2006/001940, filed on Aug. 2, 2006 which in turn claims the benefit of Chinese Application No. CN 200510089965.3, filed on Aug. 8, 2005, the disclosures of which Applications are incorporated by reference herein.

SEQUENCE LISTING

The Sequence listing in "SEQUENCE LISTING.TXT" created on Mar. 16, 2011, being 33.1 KB in size is incorporated by reference.

FIELD OF THE INVENTION

The present invention relates to biotechnology, and more specifically, relates to a two-step enzyme method for preparing 7-aminocephalosporanic acid.

BACKGROUND OF THE INVENTION

The core of many semi-synthetic cephalosporins, 7-aminocephalosporanic acid (7-ACA), can be manufactured chemically from cephalosporin C(CPC). The chemical process uses many chemical reagents that are highly toxic and heavily pollute the environment and is low in conversion rate and high in cost. Enzyme methods offer attractive alternative for production of fine chemicals without using toxic reagents and are high in conversion rate. The bioconversion of CPC to 7-ACA is conducted in two steps (FIG. 1): (1) CPC is first oxidized by D-amino acid oxidase to glutaryl-7-ACA; (2) glutaryl-7-ACA is in turn converted to 7-ACA by glutaryl-7-ACA acylase.

One of the major obstacles for large scale production of 7-ACA is the low yield and high cost of production of D-amino acid oxidase and glutaryl-7-ACA acylase. Current reports on the production level of D-amino acid oxidase is low, about 2,300 U/L fermentation medium (Pollegioni, L. et al., 1997, J. Biotechnol. 58, 115-123) and 800 U/L fermentation medium (Molla, G. et al., 1998, Protein Exp. Purif. 14, 289-294). The production level of glutaryl-7-ACA acylase production level is also low, about 129-2,500 U/L fermentation medium (Ishiye, M. and Niwa, M., 1992, Biochim. Biophys. Acta 1132, 233-239; Yang, Y. L. et al., 2001, CN1301813A; Xu, G. and Zhu, M. 2003, CN1428424A). Therefore, it is critical to produce these two enzymes for industrial production of 7-ACA at low cost.

Another obstacle for large scale production of 7-ACA resides in that existing manufacturing procedures are complex and expensive. For example, the procedures of related products by Roche Diagnostics (CC2 Twin Enzyme Process: D-AOD, product number: 1462865; Gl-Ac, product number: 1464213, Roche Diagnostics) are complicated (FIG. 1). Besides the reactions catalyzed by D-amino acid oxidase and glutaryl-7-ACA acylase, extra steps are needed: (1) due to the impurity of the D-amino acid oxidase used, a high proportion of α-ketoadipyl-7-ACA is not converted to glutaryl-7-ACA after the oxidation, thus an exogenous addition of hydrogen peroxide is required to complete the conversion; and (2) exogenous addition of catalase is required to degrade remaining hydrogen peroxide, for hydrogen peroxide can inactivate D-amino acid oxidase and oxidize CPC and glutaryl-7-ACA, thus reducing the final yield of 7-ACA.

In addition, a method to prepare 7-ACA has been published in CN1104255. In that method, since the expression vector used contained ampicillin resistance gene, the fermentation product contains β-lactamase, which significantly reduces the yield of 7-ACA and β-lactamase inhibitor is therefore required in the process. Furthermore, the host cell employed in that method produces catalase, which degrades hydrogen peroxide, therefore exogenous additions of hydrogen peroxide and catalase inhibitor are required. Consequently, the manufacturing procedures are complex and highly cost.

SUMMARY OF THE INVENTION

The object of the invention is to provide a simple, inexpensive and high yield two-step enzyme method for the preparation of 7-ACA.

To achieve the above object, the invention provides a method to prepare 7-ACA from CPC, which comprises oxidation of CPC to glutaryl-7-ACA by D-amino acid oxidase (first step reaction) and conversion of glutaryl-7-ACA to 7-ACA by glutaryl-7-ACA acylase (second step reaction). More specifically, said D-amino acid oxidase is a purified D-amino acid oxidase, with the amino acid sequence of *Trigonopsis variabilis* D-amino acid oxidase mutant as in Sequence 2 (SEQ ID NO. 2).

Preferably, said first step reaction does not require addition of hydrogen peroxide, more preferably, said D-amino acid oxidase is expressed by the expression vector pHS-GHA with the DNA sequence as in Sequence 3 (SEQ ID NO: 3). The sequential purification of D-amino acid oxidase comprises DEAE-cellulose ion exchange chromatography and ammonium sulphate precipitation. More preferably, in said first step and second step reactions, there is no addition of β-lactamase inhibitors selected from ascorbic acid, 3-amino-1,2,3-triazole, sodium perborate, and sodium azide; in said first step reaction, there is no addition of catalase inhibitors selected from sodium sulbactam, clavulanic acid, boric acid and their derivatives; in said second step reaction, there is no addition of catalase.

Preferably, said D-amino acid oxidase is immobilized, or said glutaryl-7-ACA acylase is immobilized, or both said D-amino acid oxidase and glutaryl-7-ACA acylase are immobilized.

More preferably, said glutaryl-7-ACA acylase is glutaryl-7-ACA acylase of *Pseudomonas* sp. SE83, said glutaryl-7-ACA acylase of *Pseudomonas* sp. SE83 is expressed by the expression vector pT7-kan-ACY with the DNA sequence as in Sequence 4 (SEQ ID NO: 4).

The merits of the invention comprise: (1) the purified D-amino acid oxidase mutant, with the amino acid sequence as in Sequence 2 (SEQ ID NO: 2) in the invention, possesses a specific activity of 105% higher than that of parent D-amino acid oxidase; (2) the fermentation products of the expression vectors pHS-GHA and pT7-kan-ACY of the invention do not contain β-lactamase, therefore no need to add exogenous β-lactamase inhibitor, which saves production cost and simplifies the manufacturing procedures; (3) the D-amino acid oxidase produced from the invention contains little or no catalase and therefore there is no need to add exogenous catalase inhibitor; the level of α-ketoadipyl-7-ACA is low and therefore there is no need to add exogenous hydrogen peroxide and catalase, which also reduces production cost and simplifies the manufacturing procedures; (4) the molar conversion rate of the two-step enzyme method in the invention can reach 93% or above, about 12% higher than that of the products of Roche Diagnostics (molar conversion rate is about 82%).

BRIEF DESCRIPTION OF THE DRAWINGS

FIG. 1 shows the reaction flow chart of current procedure of conversion of CPC to 7-ACA.

FIG. 2 shows expression vector pHS-GHA.

FIG. 3 shows expression vector pT7-kan-ACY.

FIG. 4 shows expression vector pRSET-lac-GI-hok/sok-kan.

FIG. 5 shows SDS-PAGE of D-amino acid oxidase GHA. Lane 1: BenchMark™ Pre-Stained Protein Ladder (Invitrogen), sizes of the proteins are in kDa; lane 2: partially purified D-amino acid oxidase GHA; lane 3: purified D-amino acid oxidase GHA.

FIG. 6 shows the HPLC chromatogram of the conversion of CPC to glutaryl-7-ACA by D-amino acid oxidase GHA.

FIG. 7 shows SDS-PAGE of glutaryl-7-ACA acylase of *Pseudomonas* sp. SE83. Lane 1: BenchMark™ Pre-Stained Protein Ladder (Invitrogen), sizes of the proteins are in kDa; lane 2: partially purified glutaryl-7-ACA acylase of *Pseudomonas* sp. SE83.

FIG. 8 shows the HPLC chromatogram of the conversion of glutaryl-7-ACA to 7-ACA by glutaryl-7-ACA acylase of *Pseudomonas* sp. SE83.

FIG. 9 shows the HPLC chromatogram of the conversion of CPC to 7-ACA by the two-step enzyme method.

EXAMPLE 1

Construction of Expression Vector pRSET-kan

The following primers were synthesized based on the sequence of pRSET-A (purchased from Invitrogen):

```
VET-F
                                          (SEQ ID NO: 8)
5'-CTGTCAGACCAAGTTTACTCATATATACTTTAG-3'

VET-R
                                          (SEQ ID NO: 9)
5'-ACTCTTCCTTTTTCAATATTATTGAAGC-3'
```

The following primers were synthesized based on the sequence of pET-28b (purchased from Novagen):

```
KAN-F
                                         (SEQ ID NO: 10)
5'-ATGAGCCATATTCAACGGGAAAC-3'

KAN-R
                                         (SEQ ID NO: 11)
5'-TTAGAAAAACTCATCGAGCATCAAATG-3'
```

PCR mixture for amplifying pRSET-A fragment devoid of ampicillin resistance gene contained: 50 ng pRSET-A (Invitrogen), 0.4 μM VET-F, 0.4 μM VET-R, 50 μM dATP, 50 μM dTTP, 50 μM dCTP, 50 μM dGTP, 20 mM Tris-HCl (pH8.8), 10 mM KCl, 10 mM $(NH_4)_2SO_4$, 2 mM $MgSO_4$, 0.1% Triton X-100, 2.5 U Pfu DNA polymerase (Promega). The volume of the mixture was made up to 50 μL with sterile deionized water.

PCR profile was as follows:

94° C., 1 min 35 cycles
94° C., 5 min → 50° C., 1 min → → → → → 72° C., 10 min
72° C., 4 min PCR mixture for amplifying kanamycin resistance gene from plasmid pET-28b contained: 50 ng pET-28b (Novagen), 0.4 μM KAN-F, 0.4 μM KAN-R, 50 μM dATP, 50 μM dTTP, 50 μM dCTP, 50 μM dGTP, 20 mM Tris-HCl (pH8.8), 10 mM KCl, 10 mM $(NH_4)_2SO_4$, 2 mM $MgSO_4$, 0.1% Triton X-100, 2.5 U Pfu DNA polymerase (Promega). The volume of the mixture was made up to 50 μL with sterile deionized water.

PCR profile was as follows:

94° C., 1 min 35 cycles
94° C., 5 min → 50° C., 1 min → → → → → 72° C., 10 min
72° C., 4 min The two PCR products (pRSET-A fragment devoid of ampicillin resistance gene, 2,036 bp in size; kanamycin resistance gene, 816 bp in size) were resolved in 0.8% agarose, purified and ligated to generate plasmid pRSET-kan. The plasmid was used to transform competent *E. coli* BL21(DE3) pLysS (Novagen), spread onto LB (1% sodium chloride, 1% peptone, 0.5% yeast extract) agar containing 50 μg/mL kanamycin and incubated at 37° C. overnight. Plasmid was extracted in accordance with Molecular Cloning—A Laboratory Manual (Sambrook, J. et al., 1989, CSHL Press).

EXAMPLE 2

Construction of Vector pRSET-lac-kan

The following primers were synthesized based on the sequence of pGEMT-Easy (Promega):

```
RBS-NdeI
                                         (SEQ ID NO: 12)
5'-CATATGTATATCTCCTTCTTGTGTGAAATTG-3'
(NdeI restriction site is underlined and ribosome
binding site is marked by broken underline);

RBS-AlwNI
                                         (SEQ ID NO: 13)
5'-CAGTGGCTGCTGCCAGTGGCGATAAGTC-3'
(AlwNI restriction site is underlined).
```

PCR was performed using pGEMT-Easy (Promega) as template to generate a 755 bp PCR product. PCR mixture contained 50 ng pGEMT-Easy (Promega), 0.4 μM RBS-NdeI, 0.4 μM RBS-AlwNI, 50 μM dATP, 50 μM dTTP, 50 μM dCTP, 50 μM dGTP, 20 mM Tris-HCl (pH8.8), 10 mM KCl, 10 mM $(NH_4)_2SO_4$, 2 mM $MgSO_4$, 0.1% Triton X-100, 2.5 U Pfu DNA polymerase (Promega). The volume of the mixture was made up to 50 μL with sterile deionized water.

PCR profile was as follows:

94° C., 1 min 35 cycles

94° C., 5 min → 50° C., 1 min → → → → → 72° C., 10 min
72° C., 4 min

The PCR product (755 bp) contains NdeI restriction site and ribosome binding site at the 5' end and AlwNI restriction site at the 3' end. The PCR product was resolved in 0.8% agarose, purified and digested by NdeI and AlwNI and then ligated with NdeI/AlwNI restricted pRSETA (Invitrogen) to generate pRSET-lac. The plasmid was used to transform competent E. coli BL21(DE3)pLysS (Novagen), spread onto LB (1% sodium chloride, 1% peptone, 0.5% yeast extract) agar containing 100 μg/mL ampicillin and incubated at 37° C. overnight. Plasmid was extracted in accordance with Molecular Cloning—A Laboratory Manual (Sambrook, J. et al., 1989, CSHL Press).

Vectors pRSET-lac and pRSET-kan were cut with AlwNI and EcoRI and resolved in 0.8% agarose, purified and ligated, generating pRSET-lac-kan. The plasmid was used to transform competent E. coli BL21(DE3)pLysS (Novagen), spread onto LB agar containing 50 μg/mL kanamycin and incubated at 37° C. overnight. Plasmid was extracted in accordance with Molecular Cloning—A Laboratory Manual (Sambrook, J. et al., 1989, CSHL Press).

EXAMPLE 3

Construction of Vector pGEMT-Easy-GI

The following primers were synthesized based on the sequence of known *Thermoanaerobacterium saccharolyticum* glucose isomerase gene (GenBank L09699).

GI-NdeI
(SEQ ID NO: 14)
5'-CATATGAATAAATATTTTGAGAACGTATCTAAAATA-3'
(NdeI restriction site is underlined);

GI-EcoRI
(SEQ ID NO: 15)
5'-GATATCTTAAGGCGCGCCTTATTCTGCAAAC-3'
(EcoRI restriction site is underlined and AscI
restriction site is double underlined).

PCR was performed using *Thermoanaerobacterium saccharolyticum* (purchased from ATCC, USA) DNA as template to generate a 1,336 bp PCR product. PCR mixture contained 50 ng *T. saccharolyticum* DNA, 0.4 μM GI-NdeI, 0.4 μM GI-EcoRI, 50 μM dATP, 50 μM dTTP, 50 μM dCTP, 50 μM dGTP, 20 mM Tris-HCl (pH8.8), 10 mM KCl, 10 mM $(NH_4)_2SO_4$, 2 mM $MgSO_4$, 0.1% Triton X-100, 2.5 U Platinum Taq High Fidelity DNA polymerase (Invitrogen). The volume of the mixture was made up to 50 μL with sterile deionized water.

PCR profile was as follows:

94° C., 1 min 35 cycles

95° C., 5 min → 50° C., 1 min → → → → → 72° C., 10 min
72° C., 3 min

The PCR product (1,336 bp) contains NdeI restriction site at the 5' end and EcoRI restriction site at the 3' end. The PCR product was resolved in 0.8% agarose, purified and ligated to pGEMT-Easy (Promega) by TA cloning, generating pGEMT-Easy-GI. The plasmid was used to transform competent E. coli DH5a (Invitrogen), spread onto LB agar containing 100 μg/mL ampicillin and incubated at 37° C. overnight. Plasmid was extracted in accordance with Molecular Cloning—A Laboratory Manual (Sambrook, J. et al., 1989, CSHL Press).

EXAMPLE 4

Construction of Vector pRSET-lac-GI-hok/sok-kan (FIG. 4)

Vector pGEMT-Easy-GI was cut by NdeI and EcoRI and resolved in 0.8% agarose, purified and ligated to NdeI/EcoRI-digested pRSET-lac-kan, generating pRSET-lac-GI-kan. The plasmid was used to transform competent E. coli BL21(DE3) pLysS (Novagen), spread onto LB agar containing 50 μg/mL kanamycin and incubated at 37° C. overnight.

Plasmid was extracted in accordance with Molecular Cloning—A Laboratory Manual (Sambrook, J. et al., 1989, CSHL Press).

Ten primers (SEQ ID NOS. 16-25) were synthesized based on known hok/sok gene sequence (GenBank X05813) (Table 1). PCR gene assembly was performed as described by Kikuchi, M. et al., 1999, Gene 236:159-167, with modifications. PCR mixture contained 20 ng each primer, 50 μM dATP, 50 μM dTTP, 50 μM dCTP, 50 μM dGTP, 20 mM Tris-HCl (pH8.8), 10 mM KCl, 10 mM $(NH_4)_2SO_4$, 2 mM $MgSO_4$, 0.1% Triton X-100, 2.5 U Pfu DNA polymerase (Promega). The volume of the mixture was made up to 50 μL with sterile deionized water.

PCR profile was as follows:

94° C., 1.5 min 30 cycles

95° C., 4 min → 50° C., 1.5 min → → → → → 72° C., 10 min
72° C., 5 min

The PCR product (580 bp) contains AscI restriction site at the 5' end and EcoRI restriction site at the 3' end. The PCR product was resolved in 0.8% agarose, cut with AscI and EcoRI and ligated to AscI/EcoRI-digested pRSET-lac-GI-kan, generating pRSET-lac-GI-hok/sok-kan. The plasmid was used to transform competent E. coli BL21(DE3)pLysS (Novagen), spread onto LB agar containing 50 μg/mL kanamycin and incubated at 37° C. overnight. Plasmid was extracted in accordance with Molecular Cloning—A Laboratory Manual (Sambrook, J. et al., 1989, CSHL Press) and sequenced as in Sequence 3 (SEQ ID NO: 3) in the Sequence Listing. Nucleotide variations were observed in some nucleotides: 1368 (C→G); 1513 (missed a T); 1804(A→T); 1826 (C→T); 2479(G→T); 2555(T→A); 3860(C→T).

TABLE 1

| Number | Primer sequence |
|---|---|
| 1 | 5'-ttggcgcgccttaagatatcaacaaac(SEQ ID NO: 16) tccgggaggcagcgtgatgcggcaacaatc acacggatttcccgtgaa-3' |
| 2 | 5'-catatacctgcacgctgaccacactca(SEQ ID NO: 17) ctttccctgaaaataatccgctcattcaga ccgttcacgggaaatccgtgtga-3' |

TABLE 1-continued

Number  Primer sequence 3  5'-ggtcagcgtgcaggtatatgggctatg(SEQ ID NO: 18)
   atgtgcccggcgcttgaggctttctgcctc
   atgacgtgaaggtggtttgttgc-3'

4  5'-cgtggtggttaatgaaaattaacttac(SEQ ID NO: 19)
   tacggggctatcttctttctgccacacaac
   acggcaacaaaccaccttcacgt-3'

5  5'-aattttcattaaccaccacgaggcatc(SEQ ID NO: 20)
   cctatgtctagtccacatcaggatagcctc
   ttaccgcgctttgcgcaaggaga-3'

6  5'-tgagacacacgatcaacacacaccaga(SEQ ID NO: 21)
   caagggaacttcgtggtagtttcatggcct
   tcttctccttgcgcaaagcgcgg-3'

7  5'-tgtgttgatcgtgtgtctcacactgtt(SEQ ID NO: 22)
   gatattcacttatctgacacgaaaatcgct
   gtgcgagattcgttacagagacg-3'

8  5'-cgcctccaggttgctacttaccggatt(SEQ ID NO: 23)
   cgtaagccatgaaagccgccacctccctgt
   gtccgtctctgtaacgaatctcg-3'

9  5'-taagtagcaacctggaggcgggcgcag(SEQ ID NO: 24)
   gcccgccttttcaggactgatgctggtctg
   actactgaagcgcctttataaag-3'

10 5'-cggaattcacaacatcagcaaggagaa(SEQ ID NO: 25)
   aggggctaccggcgaaccagcagcccctt
   ataaaggcgcttcagt-3'

EXAMPLE 5

Construction of Vector pRSET-A-DAO with Recombinant D-Amino Acid Oxidase

Primers were synthesized based on published *Trigonopsis variabilis* D-amino acid oxidase gene (Gonzalez, F. J., Montes, J., Martin, F., Lopez, M. C., Ferminan, E., Catalan, J., Galan, M. A., Dominguez, A. Molecular cloning of TvDAO1, a gene encoding a D-amino acid oxidase from *Trigonopsis variabilis* and its expression in *Saccharomyces cerevisiae* and *Kluyveromyces lactis*. Yeast 13:1399-1408, 1997).

5'-NdeI (incorporation of NdeI restriction site)
(SEQ ID NO: 26)
5'-TAGGGCTGACATATGGCTAAAATCGTTGTTATTGGTGC-3'

3'-BglII (incorporation of BglII restriction site)
(SEQ ID NO: 27)
5'-TAGGGCTGAAGATCTCTAAAGGTTTGGACGAGTAAGAGC-3'

*T. variabilis* D-amino acid oxidase gene was synthesized using the above primers, Pfu DNA polymerase (Promega) and plasmid pJL (Yang, Y. L. et al. CN1371999A) as template. Plasmid pJL contains *T. variabilis* FA10 D-amino acid oxidase gene (Li, W. et al., Acta Microbiologica Sinica 31:251-253, 1991). PCR mixture contained 40 ng pJL, 0.4 µM 5'-NdeI, 0.4 µM 3'-BglII, 50 µM dATP, 50 µM dTTP, 50 µM dCTP, 50 µM dGTP, 20 mM Tris-HCl (pH8.8), 10 mM KCl, 10 mM $(NH_4)_2SO_4$, 2 mM $MgSO_4$, 0.1% Triton X-100, 2.5 U Pfu DNA polymerase. The volume of the mixture was made up to 50 µL with sterile deionized water.

PCR profile was as follows:

94° C., 1 min 10 cycles
94° C., 5 min → 50° C., 1 min → → → → →
72° C., 2 min
94° C., 1 min 25 cycles
60° C., 1 min → → →→→ 72° C., 10 min
72° C., 2 min The PCR product (1,098 bp) contains NdeI restriction site at the 5' end and BglII restriction site at the 3' end. The PCR product was resolved in 1% agarose, purified and digested by NdeI and BglII and then ligated with 2.9 kb NdeI/BglII restricted pRSET-A (Invitrogen), generating pRSET-A-DAO. The plasmid was used to transform competent *E. coli* BL21(DE3)pLysS (Novagen), spread onto LB agar containing ampicillin and incubated at 37° C. overnight. Plasmid was extracted in accordance with Molecular Cloning—A Laboratory Manual (Sambrook, J. et al., 1989, CSHL Press) and sequenced. The DNA fragment was confirmed as *T. variabilis* D-amino acid oxidase gene as Sequence 5 (SEQ ID NO. 5) and the translated amino acid sequence as Sequence 6 (SEQ ID NO: 6).

EXAMPLE 6

Construction of Expression Vector with Recombinant D-Amino Acid Oxidase GHA

Recombinant D-amino acid oxidase GHA was constructed by site-directed mutagenesis, which was based on the procedures in PCR Protocols (Ed. John M. S. Bartlett and David Stirling, Totowa, N.J.: Humana Press, 2003).

Primers were synthesized in accordance with the sequence of cloned *T. variabilis* D-amino acid oxidase (Sequence 5, (SEQ ID NO: 5)):

Primer A
(SEQ ID NO: 28)
5'-TAGGGCTGACATATGGCTAAAATCGTTGTTATTG-3'

Primer B
(SEQ ID NO: 29)
5'-TAGGGCTGAAGATCTCTAAAGGTTTGGACGAG-3'

Primer C1
(SEQ ID NO: 30)
5'-GCAGGTGCCAACTGGCTCCCGTTTTACGATGGAGGCAAG-3'

Primer D
(SEQ ID NO: 31)
5'-GAGCCAGTTGGCACCTGCCCAAGG-3'

Primers A and B are a pair of outer primer. Primer A contains NdeI restriction site, with a portion of nucleotides overlapped with the 5'-end of the D-amino acid oxidase gene; primer B contains BglII restriction site, with a portion of nucleotides overlapped with the 3'-end of the D-amino acid oxidase gene. Primers C1 and D are inner primers. Primer C1 converts the 53rd amino acid residue of wild-type D-amino acid oxidase from threonine (Thr) to proline (Pro). Primer D contains a portion of nucleotides overlapped with primer C1.

PCR was performed, using pRSET-A-DAO as template, to synthesize fragment 1 (primers A and D) and fragment 2 (primers B and C1). PCR mixture contained: 20 ng pRSET-A-DAO, 20 mM Tris-HCl (pH8.8), 10 mM KCl, 10 mM ($NH_4$)$_2SO_4$, 2 mM $MgSO_4$, 0.1% Triton X-100, 0.4 µM primer A and 0.4 µM primer D (for synthesizing fragment 1) or 0.4 µM primer B and 0.4 µM primer C1 (for synthesizing fragment 2), 50 µM dATP, 50 µM dTTP, 50 µM dCTP, 50 µM dGTP, 1.5 U Pfu DNA polymerase. The volume of the mixture was made up to 50µ with sterile deionized water.

PCR profile was as follows:

94° C., 1 min 30 cycles
94° C., 2 min → 53° C., 1 min → → → → → 72° C., 10 min
72° C., 1 min The amplified fragment 1 and fragment 2 were resolved in and purified from 1% agarose, and used to generate full-length D-amino acid oxidase GHA gene. PCR mixture for synthesizing the full-length gene contained: 20 ng fragment 1, 20 ng fragment 2, 20 mM Tris-HCl (pH8.8), 10 mM KCl, 10 mM ($NH_4$)$_2SO_4$, 2 mM $MgSO_4$, 0.1% Triton X-100, 0.4 µM primer A and 0.4 µM primer B, 50 µM dATP, 50 µM dTTP, 50 µM dCTP, 50 µM dGTP, 1.5 U Pfu DNA polymerase. The volume of the mixture was made up to 50 µL with sterile deionized water.

PCR profile was as follows:

94° C., 1 min 35 cycles
94° C., 2 min → 53° C., 1 min → → → → → 72° C., 10 min
72° C., 2 min The full-length recombinant D-amino acid oxidase GHA gene fragment was obtained, cut with NdeI and BglII and ligated with pRSET-kan, generating pRSET-kan-DAOGHA. The plasmid was used to transform competent *E. coli* BL21 (DE3)pLysS, spread onto LB agar containing kanamycin and incubated at 37° C. overnight. Plasmid was extracted, and the insert was sequenced and confirmed as D-amino acid oxidase mutant GHA as Sequence 1 (SEQ ID NO: 1) and the translated amino acid sequence as Sequence 2 (SEQ ID NO: 2).

EXAMPLE 7

Construction of Vector pHS-GHA (FIG. 2)

Vector pRSET-kan-DAOGHA was cut by NdeI and BglII to release a DNA fragment (1,074 bp, containing D-amino acid oxidase GHA) and resolved in 0.8% agarose, purified and ligated to the large fragment of NdeI/BglII-digested pRSET-lac-GI-hok/sok-kan, generating pHS-GHA. The plasmid was used to transform competent *E. coli* BL21(DE3) pLysS (Novagen), generating clone BL-HS-GHA, spread onto LB agar containing 50 µg/mL kanamycin and incubated at 37° C. overnight. Plasmid was extracted in accordance with Molecular Cloning—A Laboratory Manual (Sambrook, J. et al., 1989, CSHL Press) and sequenced (Sequence 3, (SEQ ID NO: 3)). Nucleotide variations were observed in some nucleotides: 1390 (C→G); 1535 (missed a T); 1826(A→T); 1848 (C→T); 2501(G→T); 2577(T→A); 3882(C→T).

EXAMPLE 8

Construction of Vector pT7-kan-ACY (FIG. 3)

The following primers were synthesized based on the sequence of known glutaryl-7-ACA acylase gene of *Pseudomonas* sp. SE83 (Matsuda, A. et al., 1987, J. Bacteriol. 169, 5821-5826).

NdeI-ACY
(SEQ ID NO: 32)
5'-<u>CATATG</u>AACGCTCCCGTCCCCGTCCC-3'
(NdeI restriction site is underlined);

BglII-ACY
(SEQ ID NO: 33)
5'-<u>AGATCTT</u>CAGATGGTGAAGCGGGCAC-3'
(BglII restriction site is underlined).

PCR was performed using *Pseudomonas* sp. SE83 DNA as template to generate a 1,676 bp PCR product. PCR mixture contained 50 ng *Pseudomonas* sp. SE83 DNA, 0.4 µM NdeI-ACY, 0.4 µM BglII-ACY, 50 µM dATP, 50 µM dTTP, 50 µM dCTP, 50 µM dGTP, 20 mM Tris-HCl (pH8.8), 10 mM KCl, 10 mM ($NH_4$)$_2SO_4$, 2 mM $MgSO_4$, 0.1% Triton X-100, 2.5 U Pfu DNA polymerase (Promega). The volume of the mixture was made up to 50 µL with sterile deionized water.

PCR profile was as follows:

94° C., 1 min 35 cycles
94° C., 5 min → 50° C., 1 min → → → → → 72° C., 10 min
72° C., 3 min The PCR product (1,676 bp) contains NdeI restriction site at the 5' end and BglII restriction site at the 3' end. The PCR product was resolved in 0.8% agarose, cut with NdeI and BglII and ligated to NdeI/BglII-digested pRSET-kan, generating pT7-kan-ACY. The plasmid was used to transform competent *E. coli* BL21(DE3)pLysS (Novagen), generating clone BL-T7K-ACY, spread onto LB agar containing 50 µg/mL kanamycin and incubated at 37° C. overnight. Plasmid was extracted in accordance with Molecular Cloning—A Laboratory Manual (Sambrook, J. et al., 1989, CSHL Press) and sequenced (Sequence 4, (SEQ ID NO: 4)). Nucleotide variations were observed in four nucleotides: 2260 (G→T); 2336 (T→A); 3641(C→T); 4117(G→C).

EXAMPLE 9

Medium and Fermentation of D-Amino Acid Oxidase GHA

A single colony of clone BL-HS-GHA (Example 7) was picked from LB agar containing 50 µg/mL kanamycin and grown in 2×5 mL LB medium containing 50 µg/mL kanamycin at 37° C. for 8 hours (shaker at 250 rpm). The culture was then inoculated to 2×50 mL seed medium containing 100 µg/mL kanamycin and 40 µg/mL chloramphenicol, incubated at 30° C. for 16 hours (shaker at 400 rpm).

Preparation of Corn Steep Liquor 1:
Dissolved 300 g corn steep liquor (purchased from North China Pharmaceutical Kangxin Co., Ltd.) in 300 mL distilled water and then centrifuged (5,000 g, 8 min.) to harvest the supernatant as corn steep liquor 1. The pellet was kept for later use.

Preparation of Corn Steep Liquor 2:
Dissolved the above mentioned pellet in 600 mL distilled water and then centrifuged (5,000 g, 8 min.) to harvest the supernatant as corn steep liquor 2.

A 50 mL seed medium contained:

| | |
|---|---|
| Corn steep liquor 1 | 4 mL |
| Corn steep liquor 2 | 4 mL |
| Yeast extract | 0.2 g |
| Ammonium sulphate | 0.075 g |

-continued

| | |
|---|---|
| Disodium hydrogen phosphate | 0.25 g |
| Potassium dihydrogen phosphate | 0.04 g |
| Sodium chloride | 0.075 g |

They were dissolved in 50 mL distilled water and adjusted to pH 7.15 by 10N sodium hydroxide and sterilized by autoclaving.

After overnight incubation, the total 100 mL seed culture was inoculated to a 2 L fermentor (BIOENGINEERING, Benchtop Fermentor, KLF2000) containing 50 µg/mL kanamycin.

2 L Fermentation Medium Contained:

| | |
|---|---|
| Corn steep liquor 1 | 160 mL |
| Corn steep liquor 2 | 160 mL |
| Yeast extract | 8 g |
| Ammonium sulphate | 3 g |
| Disodium hydrogen phosphate | 10 g |
| Potassium dihydrogen phosphate | 1 g |
| Sodium chloride | 3 g |

They were dissolved in 1.9 L distilled water and adjusted to pH 7.15 by 10N sodium hydroxide and sterilized by autoclaving in the 2 L fermentor (BIOENGINEERING, Benchtop Fermentor, KLF2000).

12.5 g glucose was dissolved in 50 mL distilled water, sterilized by autoclaving; 1.25 g magnesium sulphate was dissolved in 50 mL distilled water, sterilized by autoclaving. The sterilized glucose and magnesium sulphate were added to the 2 L fermentor prior to fermentation.

Preparation of Feed:

Corn steep liquor 1 (250 mL) and corn steep liquor 2 (250 mL) were mixed and adjusted to pH 7.25 by 10N sodium hydroxide and sterilized by autoclaving.

2.25 g ammonium sulphate, 7.56 g disodium hydrogen phosphate, 1.2 g potassium dihydrogen phosphate, 2.25 g sodium chloride was dissolved in 60 mL distilled water and sterilized by autoclaving.

15 g yeast extract was dissolved in 100 mL distilled water and sterilized by autoclaving. 70 g glucose was dissolved in 140 mL distilled water and sterilized by autoclaving.

30 mL glycerol was mixed with 10 mL distilled water and sterilized by autoclaving. 20 g magnesium sulphate was dissolved in 30 mL distilled water and sterilized by autoclaving.

All solutions were mixed and kanamycin was added to final concentration of 50 µg/mL, 2 mL antifoam was added.

The fermentation was held at 35° C. In the first 6 hours, the pH value rose from 6.9 to 7.2 and the feed was started (50 mL/hour). The fermentation was proceeded for another 26 hours at controlled conditions (the pH value was maintained at 7.2 by 5N potassium hydroxide; dissolved oxygen $pO_2$ was not greater than 0.5%).

EXAMPLE 10

Partial Purification of D-Amino Acid Oxidase Mutant GHA

Fermentation was performed as in Example 9. The cells were collected by centrifugation at 4° C. (5,000 g, 8 min.), and supernatant was discarded. The wet weight of cell pellet was 220 g and it was resuspended in 600 mL sodium phosphate buffer (50 mM, pH7.5). The cells were lysed by grinding in a dynomill (DYNO-MILL TYP KDL, 0.2 mm glass beads, WA Bachofen). Cell suspension was injected into dynomill at 50 mL/min. and washed by 800 mL sodium phosphate buffer (50 mM, pH7.5). The cell lysate was heat treated at 55° C. for 30 min. in a water bath, and centrifuged (10,000 g, 30 min.). Supernatant was partial purified D-amino acid oxidase mutant GHA. The purity and concentration of the target protein was analyzed by SDS-PAGE (FIG. 5). As shown in the figure, partial purified D-amino acid oxidase mutant GHA constituted about 40% of the total soluble protein.

EXAMPLE 11

Purification of D-Amino Acid Mutant GHA

Partial purified D-amino acid oxidase mutant GHA was prepared as in Example 10 and glycerol was added to final concentration of 10% and the pH value was adjusted to 8 by 5N sodium hydroxide. The mixture was centrifuged (13,000 g, 30 min.) and the supernatant was collected. DEAE-cellulose ion exchange resin (Sigma, D-0909) was prepared in accordance with the manufacturer's instructions. The partial purified D-amino acid oxidase mutant GHA was mixed with DEAE-cellulose ion exchange resin at a ratio of 1 mL (GHA): 0.5 mL (resin) and stirred at 4° C. for 5 hours (100 rpm) and then filtered (Buchner filter funnel, 120 mm P1). The DEAE-cellulose ion exchange resin was washed by 40 mM sodium dihydrogen phosphate (with 10% glycerol) by three bed volumes, followed by 400 mM sodium dihydrogen phosphate by two bed volumes to elute D-amino acid oxidase mutant GHA. Ammonium sulphate was added (262 g/L eluted D-amino acid oxidase mutant GHA), stirred at room temperature for 15 min. and then centrifuged (13,000 g, 15 min.). Supernatant was discarded and the protein pellet was dissolved in 10 mM sodium dihydrogen phosphate (pH7.5). The purity and level of the target protein was analyzed by SDS-PAGE (FIG. 5). As shown in the figure, partial purified D-amino acid oxidase mutant GHA constituted about 90% of the total soluble protein.

EXAMPLE 12

Determination of Activity of D-Amino Acid Oxidase Mutant GHA

The procedures were performed in accordance with Isogai, T., et al, *J. Biochem. [Tokyo]* 108:10634069, 1990, with modifications. Purified D-amino acid oxidase mutant GHA was prepared as in Example 11 and diluted 10 times by sodium phosphate buffer (50 mM, pH7.5). Reaction mixture contained 2 mL 150 mM CPC sodium and 2 mL diluted purified D-amino acid oxidase mutant GHA, stirred (450 rpm) at 37° C. and the pH value was maintained at 7.5 by 5N sodium hydroxide. Aliquots (100 µL) were withdrawn at different time points (0, 15, 30, 45 min., FIG. 6), mixed with 10 µL 3% hydrogen peroxide, followed by addition of 50 µL 10% trichloroacetic acid to stop the reaction. The mixture was centrifuged (10,000 g, 3 min) and 10 µL of supernatant was mixed with 990 µL HPLC mobile phase (50 mM potassium phosphate, pH7; 5% acetonitrile), then analyzed by HPLC. HPLC column: Diamonsil™ C18, 250×4.6 mm (Diam Company, Beijing); column temperature: 30° C.; flow rate: 1 mL/min; scanning: 260 nm UV. One unit of enzyme activity was defined as the amount of enzyme that converted 1 µmole of CPC to glutary-7-ACA per min under the above reaction condition. The total activity of the D-amino acid oxidase mutant GHA was 95,607 U, which was 35,410 U/L fermentation medium.

EXAMPLE 13

Preparation of Immobilized D-Amino Acid Oxidase Mutant GHA

Purification of D-amino acid oxidase mutant GHA was performed as in Example 11. Preparation of Immobilized D-amino acid oxidase was performed in accordance with the description from Resindion S. R. L. (Italy) with modifications.

Activation of the matrix: 10 g wet Sephabeads HA was mixed with 30 mL potassium dihydrogen phosphate (100 mM, pH8) and stirred (300 rpm) at room temperature for 15 min., then the pH value was adjusted to 8 by 5N sodium hydroxide. The matrix was filtered and washed by 40 mL potassium phosphate buffer (20 mM, pH8) for 5 min. with stirring and filtered. The matrix was added with 40 mL 2% glutaraldehyde and stirred (300 rpm) at room temperature for 1 hour. The matrix was filtered and washed with 40 mL potassium phosphate (20 mM, pH8) for 5 min. and filtered. The washing was repeated 5 times and the matrix was activated.

Enzyme immobilization: The activated matrix was mixed with purified D-amino acid oxidase mutant GHA (10 g activated matrix to 100 mL purified D-amino acid oxidase mutant GHA), stirred (300 rpm) at room temperature for 1 min. The pH value was adjusted to 8 by 1N sodium hydroxide and stirred for another 18 hours. The matrix was filtered and washed by 40 mL potassium phosphate buffer (20 mM, pH8) with stirring for 2 min. and filtered. The matrix was washed by 40 mL sodium chloride (0.5M sodium chloride dissolved in 20 mM potassium phosphate buffer, pH8) for 20 min. with stirring and filtered. The washing was repeated until the eluate contained protein less than 0.1 mg/mL. The matrix was washed by 40 mL potassium phosphate buffer (20 mM, pH8) with stirring for 2 min. and filtered. The total immobilized enzyme generated was 115 g. The activity of the immobilized D-amino acid oxidase mutant GHA was determined as in Example 12, with 4 g immobilized D-amino acid oxidase mutant GHA in a reaction volume of 200 mL of 75 mM CPC sodium. The activity of the immobilized recombinant D-amino acid oxidase GHA was 77 U/g wet matrix.

EXAMPLE 14

Medium and fermentation of glutaryl-7-ACA acylase of *Pseudomonas* sp. SE83

A single colony of clone BL-T7K-ACY (Example 8) was picked from LB agar containing 50 µg/mL kanamycin and grown in 2×5 mL LB medium containing 50 µg/mL kanamycin at 37° C. for 8 hours (shaker at 250 rpm). An aliquot of culture was inoculated to 2×50 mL seed medium, incubated at 30° C. for 16 hours (shaker at 400 rpm).

A 50 mL seed medium contained:

| | |
|---|---|
| Yeast extract | 0.35 g |
| Disodium hydrogen phosphate | 0.35 g |
| Potassium dihydrogen phosphate | 0.35 g |
| Dipotassium hydrogen phosphate | 0.48 g |
| Ammonium sulphate | 0.06 g |
| Ammonium chloride | 0.01 g |

-continued

| | |
|---|---|
| Glycerol | 0.5 mL |
| Calcium chloride | 0.00055 g |

They were dissolved in 50 mL distilled water and sterilized by autoclaving.

After overnight incubation, the total 100 mL seed culture was inoculated to a 2 L fermentor (BIOENGINEERING, Benchtop Fermentor, KLF2000) containing 50 µg/mL kanamycin.

2 L fermentation medium contained:

| | |
|---|---|
| Yeast extract | 14 g |
| Disodium hydrogen phosphate | 14 g |
| Potassium dihydrogen phosphate | 14 g |
| Dipotassium hydrogen phosphate | 19.2 g |
| Ammonium sulphate | 2.4 g |
| Ammonium chloride | 0.4 g |
| Glycerol | 20 mL |
| Calcium chloride | 0.022 g |

They were dissolved in 2 L distilled water and sterilized by autoclaving in the 2 L fermentor (BIOENGINEERING, Benchtop Fermentor, KLF2000).

1 g magnesium sulphate was dissolved in 20 mL distilled water, sterilized by autoclaving; 0.14 g zinc chloride was dissolved in 20 mL distilled water, sterilized by autoclaving. The sterilized magnesium sulphate and zinc chloride were added to the 2 L fermentor prior to fermentation.

Preparation of Feed:

| | |
|---|---|
| Yeast extract | 14 g |
| Disodium hydrogen phosphate | 4.9 g |
| Potassium dihydrogen phosphate | 4.9 g |
| Dipotassium hydrogen phosphate | 6.4 g |
| Ammonium sulphate | 0.84 g |
| Ammonium chloride | 0.14 g |
| Glycerol | 175 mL |
| Calcium chloride | 0.008 g |

They were dissolved in 700 mL distilled water, sterilized by autoclaving.

0.34 g magnesium sulphate was dissolved in 20 mL distilled water, sterilized by autoclaving and added to sterilized 700 mL feed.

Kanamycin was added to final concentration of 50 µg/mL, 2 mL antifoam was added. The fermentation was held at 30° C. In the first 4 hours, the pH value was raised from 6.9 to 7.2 by 5N potassium hydroxide. Feeding was started when the $OD_{600}$ reached 4 at a feed rate of 60 mL/hour. The pH value was raised to 7.4 by 5N potassium hydroxide in the following 4 hours. IPTG (Sigma) was added to final concentration of 0.1 mM when $OD_{600}$ reached 8. The fermentation was proceeded for another 26 hours at controlled conditions (the pH value was maintained at 7.4 by 5N potassium hydroxide; dissolved oxygen $pO_2$ at 30%).

EXAMPLE 15

Partial Purification of Glutaryl-7-ACA Acylase of *Pseudomonas* sp. SE83

Fermentation was performed as in Example 14. The cells were collected by centrifugation at 4° C. (5,000 g, 8 min.), and supernatant was discarded. The wet weight of cell pellet was 130 g and it was resuspended in 400 mL sodium phosphate buffer (50 mM, pH8). The cells were lysed by grinding in the dynomill (DYNO-MILL TYP KDL, 0.2 mm glass beads, WA Bachofen). Cell suspension was injected into dynomill at 50 mL/min. and washed by 600 mL sodium phosphate buffer (50 mM, pH8). The cell lysate was heat treated at 55° C. for 15 min. in a water bath, centrifuged (10,000 g, 30 min.). Supernatant was partial purified glutaryl-7-ACA acylase of *Pseudomonas* sp. SE83. The purity and concentration of the target protein was analyzed by SDS-PAGE (FIG. 7). As shown in the figure, partial purified glutaryl-7-ACA acylase of *Pseudomonas* sp. SE83 constituted about 40% of the total soluble protein.

EXAMPLE 16

Determination of Activity of Glutaryl-7-ACA Acylase of *Pseudomonas* sp. SE83

The procedures were performed in accordance with Binder, R. et al., 1994, Appl. Environ. Microbiol. 60, 1805-1809, with modifications. The partially purified glutaryl-7-ACA acylase of *Pseudomonas* sp. SE83 (Example 15) was diluted 10 times by sodium phosphate buffer (50 mM, pH8) and mixed with same volume of 150 mM glutaryl-7-ACA (preparation as described in Shibuya, Y. et al., 1981, Agric. Biol. Chem. 45, 1561-1567) at 37° C. with continuously stirring (450 rpm) and the pH value was maintained at 8 by 5N sodium hydroxide. Aliquots (60 μL) were withdrawn at different time points (0, 15, 30, 45 min., FIG. 8) and mixed with 30 μL 10% trichloroacetic acid to stop the reaction. The mixture was centrifuged (10,000 g, 3 min.) and 10 μL of supernatant was mixed with 990 μL HPLC mobile phase (50 mM potassium phosphate, pH7; 5% acetonitrile), then analyzed by HPLC. HPLC conditions were as described in Example 12. One unit of enzyme activity was defined as the amount of enzyme that converted 1 μmole of glutaryl-7-ACA to 7-ACA per min under the above reaction condition. The total activity of the glutaryl-7-ACA acylase of *Pseudomonas* sp. SE83 was 24,822 U, about 9,570 U/L fermentation medium.

EXAMPLE 17

Preparation of Immobilized Glutaryl-7-ACA Acylase of *Pseudomonas* sp. SE83

Glutaryl-7-ACA acylase of *Pseudomonas* sp. SE83 was performed as in Example 15. Preparation of immobilized glutaryl-7-ACA acylase of *Pseudomonas* sp. SE83 was performed in accordance with the description from Röhm (Germany) with modifications. A 100 mL partially purified glutaryl-7-ACA acylase of *Pseudomonas* sp. SE83 was mixed with 10 g Eupergit C250L wet matrix, stirred (300 rpm) at room temperature for 72 hours. The matrix was filtered and washed by 100 mL distilled water at room temperature with stirring (300 rpm) for 2 min. and finally filtered by No. 3 sand funnel. The washing was repeated until the eluate contained protein less than 0.1 mg/mL. The total immobilized glutaryl-7-ACA acylase of *Pseudomonas* sp. SE83 generated was 80 g. The activity of the immobilized glutaryl-7-ACA acylase of *Pseudomonas* sp. SE83 was determined as in Example 16, with 6 g immobilized glutaryl-7-ACA acylase of *Pseudomonas* sp. SE83 in a reaction volume of 200 mL of 75 mM glutaryl-7-ACA. The activity of the immobilized glutaryl-7-ACA acylase of *Pseudomonas* sp. SE83 was 50 U/g wet matrix.

EXAMPLE 18

Two-Step Enzymatic Conversion of CPC to 7-ACA

Immobilized D-amino acid oxidase mutant GHA was prepared (40 g) as in Example 13 and added to 75 mM CPC sodium solution (1 L), stirred (250 rpm) at room temperature for 1 hour with supply of pure oxygen at a rate of 0.3 m$^3$/hour. The pH value was maintained at 7.5 by 3M ammonia. The reaction mixture was filtered and immobilized glutaryl-7-ACA acylase of *Pseudomonas* sp. SE83 (50 g, prepared as in Example 17) was added, stirred (250 rpm) at room temperature for 1 hour. The pH value was maintained at 8 by 3M ammonia. The level of 7-ACA was analyzed by HPLC as in Example 16. The HPLC chromatogram was shown in FIG. 9. As shown in FIG. 9, the whole conversion took 120 min.: after the first 60 min., most of the CPC was converted to glutaryl-7-ACA by D-amino acid oxidase mutant GHA (FIG. 9, GL-7-ACA, 60 min. peak). After another 60 min., most of the glutaryl-7-ACA was converted to 7-ACA by glutaryl-7-ACA acylase of *Pseudomonas* sp. SE83 (FIG. 9, 7-ACA, 120 min. peak). According to the HPLC data, the conversion rate of CPC to glutaryl-7-ACA was 97.96%; the conversion rate of glutaryl-7-ACA to 7-ACA was 95.78%. The conversion rate of CPC to 7-ACA by the two step enzyme method was 93.83%.

This invention is not limited by the detailed description provided in the Examples above. Various modifications can be made by those skilled in the field and these modifications should be regarded as within the scope of the claims of the invention.

We claim:

1. A method to prepare 7-aminocephalosporanic (7-ACA) from cephalosporin C (CPC), which comprises the conversion of CPC to glutaryl-7-ACA by D-amino acid oxidase (first step reaction) and the conversion of glutaryl-7-ACA to 7-ACA by glutaryl-7-ACA acylase (second step reaction), wherein said D-amino acid oxidase is a purified *Trigonopsis variabilis* D-amino acid oxidase mutant with the amino acid of SEQ ID NO: 2.

2. The method according to claim 1, in said first step reaction, hydrogen peroxide is not added.

3. The method according to claim 2, said D-amino acid oxidase is expressed from expression vector pHS-GHA with the DNA sequence of SEQ ID NO: 3.

4. The method according to claim 3, said D-amino acid oxidase is purified by sequential purifications comprising DEAE-cellulose ion exchange resin purification and ammonium sulphate precipitation.

5. The method according to claim 4, in said first step and second step reactions, β-lactamase inhibitors selected from ascorbic acid, 3-amino-1,2,3-triazole, sodium perborate, and sodium azide is not added.

6. The method according to claim 5, in said first step reaction, catalase inhibitors selected from sodium sulbactam, clavulanic acid, boric acid and their derivatives is not added.

7. The method according to claim 6, in said second step reaction, catalase is not added.

8. The method according to any of the claims 1-7, said D-amino acid oxidase is immobilized, or said glutaryl 7-aminocephalosporanic acylase (glutaryl-7-ACA acylase) is immobilized.

9. The method according to claim 8, said glutaryl-7-ACA acylase is glutaryl-7-ACA acylase of *Pseudomonas* sp. SE83.

10. The method according to claim 9, said glutaryl-7-ACA acylase of *Pseudomonas* sp. SE83 is expressed by the expression vector pT7-kan-ACY with the DNA sequence of SEQ ID NO: 4.

* * * * *

SEQUENCE LISTING

<160> NUMBER OF SEQ ID NOS: 33

<210> SEQ ID NO 1
<211> LENGTH: 1071
<212> TYPE: DNA
<213> ORGANISM: Trigonopsis variabilis

<400> SEQUENCE: 1

```
atggctaaaa tcgttgttat tggtgccggt gttgccggtt taactacagc tcttcaactt      60
cttcgtaaag gacatgaggt tacaattgtg tccgagttta cgcccggtga tcttagtatc     120
ggatatacct cgccttgggc aggtgccaac tggctcccgt tttacgatgg aggcaagtta     180
```

```
gccgactacg atgccgtctc ttatcctatc ttgcgagagc tggctcgaag cagccccgag    240
gctggaattc gactcatcaa ccaacgctcc catgttctca agcgtgatct tcctaaactg    300
gaaggtgcca tgtcggccat ctgtcaacgc aaccctggt tcaaaaacac agtcgattct     360
ttcgagatta tcgaggacag gtccaggatt gtccacgatg atgtggctta tctagtcgaa    420
tttgcttccg tttgtatcca caccggagtc tacttgaact ggctgatgtc ccaatgctta    480
tcgctcggcg ccacggtggt taaacgtcga gtgaaccata tcaaggatgc caattttcta    540
cactcctcag gatcacgccc cgacgtgatt gtcaactgta gtggtctctt gcccggttc     600 ttgggaggcg tcgaggacaa gaagatgtac cctattcgag acaagtcgt ccttgttcga     660 aactctcttc ctttttatgg ctccttttcc agcactcctg aaaaagaaaa tgaagacgaa    720
gctctatata tcatgacccg attcgatggt acttctatca ttggcggttg ttccaatcc    780 aacaactggt catccgaacc cgatccttct ctcacccatc gaatcctgtc tagagccctc    840
gaccgattcc cggaactgac caaagatggc cctcttgaca ttgtgcgcga atgcgttggc    900
caccgtcctg gtagagaggg cggtccccga gtagaattag agaagatccc cggcgttggc    960
tttgttgtcc ataactatgg tgccgccggt gctggttacc agtcctctta cggcatggct   1020
gatgaagctg tttcttacgt cgaaagagct cttactcgtc caaaccttta g            1071
```

<210> SEQ ID NO 2
<211> LENGTH: 356
<212> TYPE: PRT
<213> ORGANISM: Trigonopsis variabilis

<400> SEQUENCE: 2

```
Met Ala Lys Ile Val Val Ile Gly Ala Gly Val Ala Gly Leu Thr Thr
1               5                   10                  15

Ala Leu Gln Leu Leu Arg Lys Gly His Glu Val Thr Ile Val Ser Glu
                20                  25                  30

Phe Thr Pro Gly Asp Leu Ser Ile Gly Tyr Thr Ser Pro Trp Ala Gly
            35                  40                  45

Ala Asn Trp Leu Pro Phe Tyr Asp Gly Gly Lys Leu Ala Asp Tyr Asp
        50                  55                  60

Ala Val Ser Tyr Pro Ile Leu Arg Glu Leu Ala Arg Ser Ser Pro Glu
65                  70                  75                  80

Ala Gly Ile Arg Leu Ile Asn Gln Arg Ser His Val Leu Lys Arg Asp
                85                  90                  95

Leu Pro Lys Leu Glu Gly Ala Met Ser Ala Ile Cys Gln Arg Asn Pro
            100                 105                 110

Trp Phe Lys Asn Thr Val Asp Ser Phe Glu Ile Ile Glu Asp Arg Ser
        115                 120                 125

Arg Ile Val His Asp Asp Val Ala Tyr Leu Val Glu Phe Ala Ser Val
130                 135                 140

Cys Ile His Thr Gly Val Tyr Leu Asn Trp Leu Met Ser Gln Cys Leu
145                 150                 155                 160

Ser Leu Gly Ala Thr Val Val Lys Arg Arg Val Asn His Ile Lys Asp
                165                 170                 175

Ala Asn Phe Leu His Ser Ser Gly Ser Arg Pro Asp Val Ile Val Asn
            180                 185                 190

Cys Ser Gly Leu Phe Ala Arg Phe Leu Gly Gly Val Glu Asp Lys Lys
        195                 200                 205

Met Tyr Pro Ile Arg Gly Gln Val Val Leu Val Arg Asn Ser Leu Pro
210                 215                 220
```

```
Phe Met Ala Ser Phe Ser Ser Thr Pro Glu Lys Glu Asn Glu Asp Glu
225                 230                 235                 240

Ala Leu Tyr Ile Met Thr Arg Phe Asp Gly Thr Ser Ile Ile Gly Gly
            245                 250                 255

Cys Phe Gln Ser Asn Asn Trp Ser Ser Glu Pro Asp Pro Ser Leu Thr
        260                 265                 270

His Arg Ile Leu Ser Arg Ala Leu Asp Arg Phe Pro Glu Leu Thr Lys
    275                 280                 285

Asp Gly Pro Leu Asp Ile Val Arg Glu Cys Val Gly His Arg Pro Gly
        290                 295                 300

Arg Glu Gly Gly Pro Arg Val Glu Leu Glu Lys Ile Pro Gly Val Gly
305                 310                 315                 320

Phe Val Val His Asn Tyr Gly Ala Ala Gly Ala Gly Tyr Gln Ser Ser
                325                 330                 335

Tyr Gly Met Ala Asp Glu Ala Val Ser Tyr Val Glu Arg Ala Leu Thr
            340                 345                 350

Arg Pro Asn Leu
        355

<210> SEQ ID NO 3
<211> LENGTH: 4723
<212> TYPE: DNA
<213> ORGANISM: Artificial
<220> FEATURE:
<223> OTHER INFORMATION: Expression Vector pHS-GHA

<400> SEQUENCE: 3
catatggcta aatcgttgt tattggtgcc ggtgttgccg gtttaactac agctcttcaa      60
cttcttcgta aaggacatga ggttacaatt gtgtccgagt ttacgcccgg tgatcttagt    120
atcggatata cctcgccttg ggcaggtgcc aactggctcc cgttttacga tggaggcaag    180
ttagccgact acgatgccgt ctcttatcct atcttgcgag agctggctcg aagcagcccc    240
gaggctggaa ttcgactcat caaccaacgc tcccatgttc tcaagcgtga tcttcctaaa    300
ctggaaggtg ccatgtcggc catctgtcaa cgcaaacccct ggttcaaaaa cacagtcgat   360
tctttcgaga ttatcgagga caggtccagg attgtccacg atgatgtggc ttatctagtc    420
gaatttgctt ccgttttgtat ccacaccgga gtctacttga actggctgat gtcccaatgc   480
ttatcgctcg gcgccacggt ggttaaacgt cgagtgaacc atatcaagga tgccaatttt    540
ctacactcct caggatcacg ccccgacgtg attgtcaact gtagtggtct ctttgccccgg   600 ttcttgggag gcgtcgagga caagaagatg taccctattc gaggacaagt cgtccttgtt    660
cgaaactctc ttcctttat ggcctccttt tccagcactc ctgaaaaaga aaatgaagac    720
gaagctctat atatcatgac ccgattcgat ggtacttcta tcattggcgg ttgtttccaa    780
tccaacaact ggtcatccga acccgatcct ctctcaccc atcgaatcct gtctagagcc    840
ctcgaccgat tcccggaact gaccaaagat ggccctcttg acattgtgcg cgaatgcgtt    900
ggccaccgtc ctggtagaga gggcggtccc cgagtagaat tagagaagat ccccggcgtt    960
ggctttgttg tccataacta tggtgccgcc ggtgctggtt accagtcctc ttacggcatg   1020
gctgatgaag ctgttcttta cgtcgaaaga gctcttactc gtccaaacct ttagagatct   1080
tttcttaggt cacatagcag gaatggatgc ttttgcaaaa ggctttaaag ttgcttacaa   1140
gcttgtgaaa gatggcgtat ttgacaagtt catcgaagaa agatacgcaa gctacaaaga   1200
aggcattggc gctgatattg taagcggtaa agctgacttc aagagccttg aaaagtatgc   1260
attagagcac agccagattg taaacaaatc aggcagacaa gagctattag aatcaatcct   1320
```

```
aaatcagtat ttgttttgcag aataaggcgc gccttaagat atcaacaaac tccgggaggc    1380
agcgtgatgg ggcaacaatc acacggattt cccgtgaacg gtctgaatga gcggattatt    1440
ttcagggaaa gtgagtgtgg tcagcgtgca ggtatatggg ctatgatgtg cccggcgctt    1500
gaggctttct gcctcatgac gtgaaggtgg tttgtgccgt gttgtgtggc agaaagaaga    1560 tagcccccgta gtaagttaat tttcattaac caccacgagg catccctatg tctagtccac    1620
atcaggatag cctcttaccg cgctttgcgc aaggagaaga aggccatgaa actaccacga    1680
agttcccttg tctggtgtgt gttgatcgtg tgtctcacac tgttgatatt cacttatctg    1740
acacgaaaat cgctgtgcga gattcgttac agagacggac acagggaggt ggcggctttc    1800
atggcttacg aatccggtaa gtagctacct ggaggcgggc gcaggcctgc cttttcagga    1860
ctgatgctgg tctgactact gaagcgcctt tataaagggg ctgctggttc gccggtagcc    1920
cctttctcct tgctgatgtt gtgaattcga agcttgatcc ggctgctaac aaagcccgaa    1980
aggaagctga gttggctgct gccaccgctg agcataacta gcataaccc cttggggcct    2040 ctaaacgggt cttgagggt ttttgctga aggaggaac tatatccgga tctggcgtaa    2100
tagcgaagag gcccgcaccg atcgcccttc ccaacagttg cgcagcctga atggcgaatg    2160
ggacgcgccc tgtagcggcg cattaagcgc ggcgggtgtg gtggttacgc gcagcgtgac    2220
cgctacactt gccagcgccc tagcgcccgc tcctttcgct ttcttccctt cctttctcgc    2280
cacgttcgcc ggctttcccc gtcaagctct aaatcggggg ctcccttag ggttccgatt    2340 tagtgcttta cggcacctcg accccaaaaa acttgattag ggtgatggtt cacgtagtgg    2400
gccatcgccc tgatagacgg ttttttcgccc tttgacgttg gagtccacgt tctttaatag    2460
tggactcttg ttccaaactg gaacaacact caacccctatc tcggtctatt cttttgattt    2520
ataagggatt ttgccgattt cggcctattg gttaaaaaat gagctgattt aacaaaaatt    2580
taacgcgaat tttaacaaaa tattaacgct tacaatttag gtggcacttt tcggggaaat    2640
gtgcgcggaa cccctatttg ttatttttc taaatacatt caaatatgta tccgctcatg    2700
agacaataac cctgataaat gcttcaataa tattgaaaaa ggaagagtat gagtcatatt    2760
caacgggaaa cgtcttgctc taggccgcga ttaaattcca acatggatgc tgatttatat    2820
gggtataaat gggctcgcga taatgtcggg caatcaggtg cgacaatcta tcgattgtat    2880
gggaagcccg atgcgccaga gttgtttctg aaacatggca aaggtagcgt tgccaatgat    2940
gttacagatg agatggtcag actaaactgg ctgacggaat ttatgcctct tccgaccatc    3000
aagcatttta tccgtactcc tgatgatgca tggttactca ccactgcgat ccccgggaaa    3060
acagcattcc aggtattaga agaatatcct gattcaggtg aaaatattgt tgatgcgctg    3120
gcagtgttcc tgcgccggtt gcattcgatt cctgtttgta attgtccttt taacagcgat    3180
cgcgtatttc gtctcgctca ggcgcaatca cgaatgaata acggtttggt tgatgcgagt    3240
gattttgatg acgagcgtaa tggctggcct gttgaacaag tctggaaaga atgcataaa    3300 cttttgccat tctcaccgga ttcagtcgtc actcatggtg atttctcact tgataacctt    3360 attttttgacg aggggaaatt aataggttgt attgatgttg gacgagtcgg aatcgcagac    3420
cgataccagg atcttgccat cctatggaac tgcctcggtg agttttctcc ttcattacag    3480
aaacggcttt ttcaaaaata tggtattgat aatcctgata tgaataaatt gcagtttcat    3540
ttgatgctcg atgagttttt ctaactgtca gaccaagttt actcatatat actttagatt    3600
gatttaaaac ttcattttta atttaaaagg atctaggtga agatccttt tgataatctc    3660 atgaccaaaa tcccttaacg tgagttttcg ttccactgag cgtcagaccc cgtagaaaag    3720
```

| | |
|---|---|
| atcaaaggat cttcttgaga tcctttttt ctgcgcgtaa tctgctgctt gcaaacaaaa | 3780 |
| aaaccaccgc taccagcggt ggtttgtttg ccggatcaag agctaccaac tcttttttccg | 3840 |
| aaggtaactg gcttcagcag agcgcagata ccaaatactg ttcttctagt gtagccgtag | 3900 |
| ttaggccacc acttcaagaa ctctgtagca ccgcctacat acctcgctct gctaatcctg | 3960 |
| ttaccagtgg ctgctgccag tggcgataag tcgtgtctta ccgggttgga ctcaagacga | 4020 |
| tagttaccgg ataaggcgca gcggtcgggc tgaacggggg gttcgtgcac acagcccagc | 4080 |
| ttggagcgaa cgacctacac cgaactgaga tacctacagc gtgagctatg agaaagcgcc | 4140 |
| acgcttcccg aagggagaaa ggcggacagg tatccggtaa gcggcagggt cggaacagga | 4200 |
| gagcgcacga gggagcttcc agggggaaac gcctggtatc tttatagtcc tgtcgggttt | 4260 |
| cgccacctct gacttgagcg tcgatttttg tgatgctcgt caggggggcg gagcctatgg | 4320 |
| aaaaacgcca gcaacgcggc cttttacgg ttcctggcct tttgctggcc ttttgctcac | 4380 |
| atgttctttc ctgcgttatc ccctgattct gtggataacc gtattaccgc ctttgagtga | 4440 |
| gctgataccg ctcgccgcag ccgaacgacc gagcgcagcg agtcagtgag cgaggaagcg | 4500 |
| gaagagcgcc caatacgcaa accgcctctc ccgcgcgtt ggccgattca ttaatgcagc | 4560 |
| tggcacgaca ggtttcccga ctggaaagcg ggcagtgagc gcaacgcaat taatgtgagt | 4620 |
| tagctcactc attaggcacc ccaggcttta cactttatgc ttccggctcg tatgttgtgt | 4680 |
| ggaattgtga gcggataaca atttcacaca agaaggagat ata | 4723 |

<210> SEQ ID NO 4
<211> LENGTH: 4414
<212> TYPE: DNA
<213> ORGANISM: Artificial
<220> FEATURE:
<223> OTHER INFORMATION: Expression Vector pT7-kan-ACY

<400> SEQUENCE: 4

| | |
|---|---|
| catatgaacg ctcccgtccc cgtcccgcgc gtcgccgatt tcacctgcga gaagaagcct | 60 |
| gcgagcggct cgcgcggcat ggtcgtcacc aaccaccgc tcgcctcggc agccggcgcg | 120 |
| cagatcctgc tcgccggcgg caatgccatc gacgcggctg tcgcgtcgct cttcgcgctg | 180 |
| acggtggccg agccgatgat ggtcggcatc ctcggcgggg gcctgagcca tatccggctc | 240 |
| gccgacgggc gtcatgtcgt gatcgacaat ctctcgaccg cgccgggcaa ggcgacggcc | 300 |
| gagatgtacg agtgcctgtc cgacgagatc ggcaagcagc gcgacacgcg cgaccgccag | 360 |
| aacgtggtcg agccaaggc ggtcgcggtt cccggcgcgc tcaagggctg gtgcgaggcg | 420 |
| ctcgcccgct tcggcacgct gccgctcgcc gaggttctcc agccggcgat cgggctggcg | 480 |
| gagcgcggct tcgtggtcac gccctatctc tcgaactgca tcaccgacaa cgcgggcgat | 540 |
| ctcgcccgcg accccggcct cgcggcgatg ctgctgccgg gcggaaagcc gctccagccg | 600 |
| ggcatgcggc tcgtccagtc cgactatgcc gcgagcctca aactgatcgc ggctgagggg | 660 |
| ccggacgcgc tctatggcgg caagctcggc cgggcgctga ccgattacat ggcggccaat | 720 |
| ggcggcctga tcgatcaggc cgacctcgcc aattaccgca tcgaactgcg cgagccgatt | 780 |
| cgcggctcct atcgcggcta cgagatcatc ggcccgccgc cgccctcgtc atcgggcgtg | 840 |
| catatcacgc agatgctcaa cattctcgaa ggctatgata tcggctcgct cggcttcggc | 900 |
| tcgacggacg ctgtgcatct gctcgccgaa gccctgaaga tcgccttcgc cgaccgcgcc | 960 |
| gtggcgacag ccgatccggc cttcgtcaag gttccggtcg cgcgattgat cgacaaggcc | 1020 |
| tatgccgacg agcgccgcgc gctcattgag atggagcagg cgaagagctg gacggccggg | 1080 |

```
ctctctggcg gcgaatccgc cgacaccact catgtcaccg tcgctgacgc catggggaat    1140
gtcgtcagcg cgacgcagac gatcaacggg ctgttcggcg cctgcgtgca gattccgggc    1200
accggcatga tcgccaacaa ctacatgtac aacttcgatc cgcatcccgg ccgggcgctc    1260
tcgatcgcgc cgggaaagag ggtcttcacc tcgatggcgc cgatgatggc gttgaaggag    1320
ggacggatcg cctttgcgct cggcttgcct ggcgcgctcc gcatcttccc ctcggcgctg    1380
caggcgatcg tcaacctgat cgaccaccgc atgagcctgc aggaggcggt cgaggcgcca    1440
cgcgtctgga cggagggcgg cgtgctcgaa ctcgaggaag cgatccccga ggccgtggca    1500
caagcgctga tcgcgcgcgg ccataaggtg gtgcgctcgc cccgcgtggc cggtggcatg    1560
aacgccatcg ccttcaatcc ggacggtacc ttgaccggtg ccgcctgctg gcgcgccgac    1620
ggcacacccg tcgccatctc cggcgggctc gcccgtgccg gtgcccgctt caccatctga    1680
agatctgcag ctggtaccat ggaattcgaa gcttgatccg gctgctaaca aagcccgaaa    1740
ggaagctgag ttggctgctg ccaccgctga gcaataacta gcataacccc ttggggcctc    1800
taaacgggtc ttgaggggtt ttttgctgaa aggaggaact atatccggat ctggcgtaat    1860
agcgaagagg cccgcaccga tcgcccttcc caacagttgc gcagcctgaa tggcgaatgg    1920
gacgcgccct gtagcggcgc attaagcgcg gcgggtgtgg tggttacgcg cagcgtgacc    1980
gctacacttg ccagcgccct agcgcccgct cctttcgctt tcttcccttc ctttctcgcc    2040
acgttcgccg gctttccccg tcaagctcta aatcgggggc tccctttagg gttccgattt    2100
agtgctttac ggcacctcga cccaaaaaaa cttgattagg gtgatggttc acgtagtggg    2160
ccatcgccct gatagacggt ttttcgccct ttgacgttgg agtccacgtt ctttaatagt    2220
ggactcttgt tccaaactgg aacaacactc aaccctatct cggtctattc ttttgattta    2280
taagggattt tgccgatttc ggcctattgg ttaaaaaatg agctgattta caaaaatttt    2340
aacgcgaatt ttaacaaaat attaacgctt acaatttagg tggcacttttt cggggaaatg    2400 tgcgcggaac ccctatttgt ttatttttct aaatacattc aaatatgtat ccgctcatga    2460
gacaataacc ctgataaatg cttcaataat attgaaaaag gaagagtatg agtcatattc    2520
aacgggaaac gtcttgctct aggccgcgat taaattccaa catggatgct gatttatatg    2580
ggtataaatg ggctcgcgat aatgtcgggc aatcaggtgc gacaatctat cgattgtatg    2640
ggaagcccga tgcgccagag ttgtttctga acatggcaa aggtagcgtt gccaatgatg    2700
ttacagatga gatggtcaga ctaaactggc tgacggaatt tatgcctctt ccgaccatca    2760
agcattttat ccgtactcct gatgatgcat ggttactcac cactgcgatc cccgggaaaa    2820
cagcattcca ggtattagaa gaatatcctg attcaggtga aaatattgtt gatgcgctgg    2880
cagtgttcct gcgccggttg cattcgattc ctgtttgtaa ttgtccttttt aacagcgatc    2940 gcgtatttcg tctcgctcag gcgcaatcac gaatgaataa cggtttggtt gatgcgagtg    3000
attttgatga cgagcgtaat ggctggcctg ttgaacaagt ctggaaagaa atgcataaac    3060
ttttgccatt ctcaccggat tcagtcgtca ctcatggtga tttctcactt gataaaccttta    3120 tttttgacga ggggaaatta ataggttgta ttgatgttgg acgagtcgga atcgcagacc    3180
gataccagga tcttgccatc ctatggaact gcctcggtga ttttctcctt cattacagaa    3240
aacggctttt tcaaaaatat ggtattgata atcctgatat gaataaattg cagtttcatt    3300
tgatgctcga tgagttttttc taactgtcag accaagttta ctcatatata ctttagattg    3360
atttaaaact tcatttttaa tttaaaagga tctaggtgaa gatcctttttt gataatctca    3420 tgaccaaaat cccttaacgt gagttttcgt tccactgagc gtcagacccc gtagaaaaga    3480
```

```
tcaaaggatc ttcttgagat cctttttttc tgcgcgtaat ctgctgcttg caaacaaaaa    3540
aaccaccgct accagcggtg gtttgtttgc cggatcaaga gctaccaact cttttttccga   3600 aggtaactgg cttcagcaga gcgcagatac caaatactgt tcttctagtg tagccgtagt    3660
taggccacca cttcaagaac tctgtagcac cgcctacata cctcgctctg ctaatcctgt    3720
taccagtggc tgctgccagt ggcgataagt cgtgtcttac cgggttggac tcaagacgat    3780
agttaccgga taaggcgcag cggtcgggct gaacggggg ttcgtgcaca cagcccagct     3840
tggagcgaac gacctacacc gaactgagat acctacagcg tgagctatga aaagcgcca    3900 cgcttcccga agggagaaag gcggacaggt atccggtaag cggcagggtc ggaacaggag   3960
agcgcacgag ggagcttcca gggggaaacg cctggtatct ttatagtcct gtcgggtttc   4020
gccacctctg acttgagcgt cgattttgt gatgctcgtc aggggggcgg agcctatgga    4080
aaaacgccag caacgcggcc ttttacggt tcctggcctt ttgctggcct tttgctcaca    4140 tgttcttcc tgcgttatcc cctgattctg tggataaccg tattaccgcc tttgagtgag    4200
ctgataccgc tcgccgcagc cgaacgaccg agcgcagcga gtcagtgagc gaggaagcgg   4260
aagagcgccc aatacgcaaa ccgcctctcc ccgcgcgttg gccgattcat taatgcagga   4320
tctcgatccc gcgaaattaa tacgactcac tataggagag ccacaacggt ttccctctag   4380
aaataatttt gtttaacttt aagaaggaga tata                                4414
```

<210> SEQ ID NO 5
<211> LENGTH: 1071
<212> TYPE: DNA
<213> ORGANISM: Trigonopsis variabilis

<400> SEQUENCE: 5

```
atggctaaaa tcgttgttat tggtgccggt gttgccggtt aactacagc tcttcaactt      60 cttcgtaaag gacatgaggt tacaattgtg tccgagttta cgcccggtga tcttagtatc    120
ggatatacct cgccttgggc aggtgccaac tggctcacat tttacgatgg aggcaagtta    180
gccgactacg atgccgtctc ttatcctatc ttgcgagagc tggctcgaag cagccccgag    240
gctggaattc gactcatcaa ccaacgctcc catgttctca agcgtgatct tcctaaactg    300
gaaggtgcca tgtcggccat ctgtcaacgc aaccccctggt tcaaaaacac agtcgattct    360
ttcgagatta tcgaggacag gtccaggatt gtccacgatg atgtggctta tctagtcgaa    420
tttgcttccg tttgtatcca caccggagtc tacttgaact ggctgatgtc ccaatgctta    480
tcgctcggcg ccacggtggt taaacgtcga gtgaaccata tcaaggatgc caattttcta    540
cactcctcag gatcacgccc cgacgtgatt gtcaactgta gtggtctctt tgcccggttc    600
ttgggaggcg tcgaggacaa gaagatgtac cctattcgag acaagtcgt ccttgttcga    660 aactctcttc ttttatggc ctccttttcc agcactcctg aaaaagaaaa tgaagacgaa    720
gctctatata tcatgacccg attcgatggt acttctatca ttggcggttg tttccaatcc    780
aacaactggt catccgaacc cgatccttct ctcacccatc gaatcctgtc tagagccctc    840
gaccgattcc cggaactgac caaagatggc cctcttgaca ttgtgcgcga atgcgttggc    900
caccgtcctg gtagagaggg cggtcccccga gtagaattag agaagatccc cggcgttggc    960
tttgttgtcc ataactatgg tgccgccggt gctggttacc agtcctctta cggcatggct    1020
gatgaagctg tttcttacgt cgaaagagct cttactcgtc caaacccttta g            1071
```

<210> SEQ ID NO 6
<211> LENGTH: 356

```
<212> TYPE: PRT
<213> ORGANISM: Trigonopsis variabilis

<400> SEQUENCE: 6

Met Ala Lys Ile Val Val Ile Gly Ala Gly Val Ala Gly Leu Thr Thr
1               5                   10                  15

Ala Leu Gln Leu Leu Arg Lys Gly His Glu Val Thr Ile Val Ser Glu
            20                  25                  30

Phe Thr Pro Gly Asp Leu Ser Ile Gly Tyr Thr Ser Pro Trp Ala Gly
        35                  40                  45

Ala Asn Trp Leu Thr Phe Tyr Asp Gly Gly Lys Leu Ala Asp Tyr Asp
    50                  55                  60

Ala Val Ser Tyr Pro Ile Leu Arg Glu Leu Ala Arg Ser Ser Pro Glu
65                  70                  75                  80

Ala Gly Ile Arg Leu Ile Asn Gln Arg Ser His Val Leu Lys Arg Asp
                85                  90                  95

Leu Pro Lys Leu Glu Gly Ala Met Ser Ala Ile Cys Gln Arg Asn Pro
            100                 105                 110

Trp Phe Lys Asn Thr Val Asp Ser Phe Glu Ile Ile Glu Asp Arg Ser
        115                 120                 125

Arg Ile Val His Asp Asp Val Ala Tyr Leu Val Glu Phe Ala Ser Val
    130                 135                 140

Cys Ile His Thr Gly Val Tyr Leu Asn Trp Leu Met Ser Gln Cys Leu
145                 150                 155                 160

Ser Leu Gly Ala Thr Val Val Lys Arg Arg Val Asn His Ile Lys Asp
                165                 170                 175

Ala Asn Phe Leu His Ser Ser Gly Ser Arg Pro Asp Val Ile Val Asn
            180                 185                 190

Cys Ser Gly Leu Phe Ala Arg Phe Leu Gly Gly Val Glu Asp Lys Lys
        195                 200                 205

Met Tyr Pro Ile Arg Gly Gln Val Val Leu Val Arg Asn Ser Leu Pro
    210                 215                 220

Phe Met Ala Ser Phe Ser Ser Thr Pro Glu Lys Glu Asn Glu Asp Glu
225                 230                 235                 240

Ala Leu Tyr Ile Met Thr Arg Phe Asp Gly Thr Ser Ile Ile Gly Gly
                245                 250                 255

Cys Phe Gln Ser Asn Asn Trp Ser Ser Glu Pro Asp Pro Ser Leu Thr
            260                 265                 270

His Arg Ile Leu Ser Arg Ala Leu Asp Arg Phe Pro Glu Leu Thr Lys
        275                 280                 285

Asp Gly Pro Leu Asp Ile Val Arg Glu Cys Val Gly His Arg Pro Gly
    290                 295                 300

Arg Glu Gly Gly Pro Arg Val Glu Leu Glu Lys Ile Pro Gly Val Gly
305                 310                 315                 320

Phe Val Val His Asn Tyr Gly Ala Ala Gly Ala Gly Tyr Gln Ser Ser
                325                 330                 335

Tyr Gly Met Ala Asp Glu Ala Val Ser Tyr Val Glu Arg Ala Leu Thr
            340                 345                 350

Arg Pro Asn Leu
        355

<210> SEQ ID NO 7
<211> LENGTH: 4701
<212> TYPE: DNA
<213> ORGANISM: Artificial
<220> FEATURE:
```

<223> OTHER INFORMATION: Vector pRSET-lac-GI-hok/sok-kan

<400> SEQUENCE: 7

| | | | | | |
|---|---|---|---|---|---|
| catatgaata | aatattttga | gaacgtatct | aaaataaaat | atgaaggacc | aaaatcaaat | 60 |
| aatccttatt | cctttaaatt | ttacaatcca | gaggaagtaa | tcgatggcaa | gacgatggag | 120 |
| gagcatctcc | gcttttctat | agcttattgg | cacactttta | ctgctgatgg | aacagatcaa | 180 |
| tttggcaagg | ctactatgca | aagaccatgg | aaccactaca | cagatcctat | ggatatagcg | 240 |
| aaagcaaggg | tagaagcagc | atttgagttt | tttgataaga | taaatgcacc | tttcttctgc | 300 |
| ttccatgata | gggatattgc | ccctgaagga | gatactctta | gagagacaaa | caaaaactta | 360 |
| gatacaatag | ttgctatgat | aaaggattac | ttaaagacca | gcaagacaaa | agttttgttt | 420 |
| ggtaccgcaa | atcttttctc | caatccgaga | tttgtacatg | gtgcatcaac | atcctgcaat | 480 |
| gctgacgttt | ttgcatattc | tgcagcgcaa | gtcaaaaaag | cccttgagat | tactaaggag | 540 |
| cttggcccgg | aaaactacgt | attttggggt | ggaagagaag | ggtacgagac | gcttctcaat | 600 |
| acagatatgg | agttagagct | tgataacttt | gcaagatttt | tgcacatggc | tgttgactat | 660 |
| gcaaaggaaa | tcggctttga | aggtcagttc | ttgattgagc | cgaagccaaa | ggagcctaca | 720 |
| aaacatcaat | acgactttga | cgtggcaaat | gtattggcat | tcttgagaaa | atacgacctt | 780 |
| gacaaatatt | tcaaagtaaa | tatcgaagca | aaccatgcga | cattggcatt | ccacgacttc | 840 |
| caacatgagc | taagatacgc | cagaataaac | ggtgtattag | gatcaattga | cgcaaatcaa | 900 |
| ggcgacatgc | ttttgggatg | ggatacggac | cagttcccta | cagatatacg | catgacaacg | 960 |
| cttgctatgt | atgaagtcat | aaagatgggt | ggatttgaca | aaggtggcct | taactttgat | 1020 |
| gcaaagtaa | gacgtgcttc | atttgagcca | gaagatcttt | tcttaggtca | catagcagga | 1080 |
| atggatgctt | ttgcaaaagg | ctttaaagtt | gcttacaagc | ttgtgaaaga | tggcgtattt | 1140 |
| gacaagttca | tcgaagaaag | atacgcaagc | tacaaagaag | gcattggcgc | tgatattgta | 1200 |
| agcggtaaag | ctgacttcaa | gagccttgaa | aagtatgcat | tagagcacag | ccagattgta | 1260 |
| aacaaatcag | gcagacaaga | gctattagaa | tcaatcctaa | atcagtattt | gtttgcagaa | 1320 |
| taaggcgcgc | cttaagatat | caacaaactc | cgggaggcag | cgtgatgggg | caacaatcac | 1380 |
| acggatttcc | cgtgaacggt | ctgaatgagc | ggattatttt | cagggaaagt | gagtgtggtc | 1440 |
| agcgtgcagg | tatatgggct | atgatgtgcc | cggcgcttga | ggcttctgc | ctcatgacgt | 1500 |
| gaaggtggtt | tgtgccgtgt | tgtgtggcag | aaagaagata | gccccgtagt | aagttaattt | 1560 |
| tcattaacca | ccacgaggca | tcccctatgtc | tagtccacat | caggatagcc | tcttaccgcg | 1620 |
| ctttgcgcaa | ggagaagaag | gccatgaaac | taccacgaag | ttcccttgtc | tggtgtgtgt | 1680 |
| tgatcgtgtg | tctcacactg | ttgatattca | cttatctgac | acgaaaatcg | ctgtgcgaga | 1740 |
| ttcgttacag | agacggacac | agggaggtgg | cggctttcat | ggcttacgaa | tccggtaagt | 1800 |
| agctacctgg | aggcgggcgc | aggcctgcct | tttcaggact | gatgctggtc | tgactactga | 1860 |
| agcgccttta | taagggggct | gctggttcgc | cggtagcccc | tttctccttg | ctgatgttgt | 1920 |
| gaattcgaag | cttgatccgg | ctgctaacaa | agcccgaaag | gaagctgagt | tggctgctgc | 1980 |
| caccgctgag | caataactag | cataaccccct | tggggcctct | aaacgggtct | tgagggggttt | 2040 |
| tttgctgaaa | ggaggaacta | tatccggatc | tggcgtaata | gcgaagaggc | ccgcaccgat | 2100 |
| cgcccttccc | aacagttgcg | cagcctgaat | ggcgaatggg | acgcgccctg | tagcggcgca | 2160 |
| ttaagcgcgg | cgggtgtggt | ggttacgcgc | agcgtgaccg | ctacacttgc | cagcgcccta | 2220 |
| gcgcccgctc | ctttcgcttt | cttccctctcc | tttctcgcca | cgttcgccgg | ctttccccgt | 2280 |

```
caagctctaa atcgggggct ccctttaggg ttccgattta gtgctttacg gcacctcgac    2340
cccaaaaaac ttgattaggg tgatggttca cgtagtgggc catcgccctg atagacggtt    2400
tttcgcccct tgacgttgga gtccacgttc tttaatagtg gactcttgtt ccaaactgga    2460
acaacactca accctatctc ggtctattct tttgatttat aagggatttt gccgatttcg    2520
gcctattggt taaaaaatga gctgatttaa caaaaattta acgcgaattt taacaaaata    2580
ttaacgctta caatttaggt ggcacttttc ggggaaatgt gcgcggaacc cctatttgtt    2640
tatttttcta aatacattca aatatgtatc cgctcatgag acaataaccc tgataaatgc    2700
ttcaataata ttgaaaaagg aagagtatga gtcatattca acgggaaacg tcttgctcta    2760
ggccgcgatt aaattccaac atggatgctg atttatatgg gtataaatgg gctcgcgata    2820
atgtcgggca atcaggtgcg acaatctatc gattgtatgg gaagcccgat gcgccagagt    2880
tgtttctgaa acatggcaaa ggtagcgttg ccaatgatgt tacagatgag atggtcagac    2940
taaactggct gacggaattt atgcctcttc cgaccatcaa gcattttatc cgtactcctg    3000
atgatgcatg gttactcacc actgcgatcc ccgggaaaac agcattccag gtattagaag    3060
aatatcctga ttcaggtgaa atattgttg atgcgctggc agtgttcctg cgccggttgc    3120
attcgattcc tgtttgtaat tgtccttta acagcgatcg cgtatttcgt ctcgctcagg    3180
cgcaatcacg aatgaataac ggtttggttg atgcgagtga ttttgatgac gagcgtaatg    3240
gctggcctgt tgaacaagtc tggaaagaaa tgcataaact tttgccattc tcaccggatt    3300
cagtcgtcac tcatggtgat ttctcacttg ataaccttat ttttgacgag gggaaattaa    3360
taggttgtat tgatgttgga cgagtcggaa tcgcagaccg ataccaggat cttgccatcc    3420
tatggaactg cctcggtgag ttttctcctt cattacagaa acggcttttt caaaaatatg    3480
gtattgataa tcctgatatg aataaattgc agtttcattt gatgctcgat gagttttttct    3540 aactgtcaga ccaagtttac tcatatatac tttagattga tttaaaactt catttttaat    3600
ttaaaaggat ctaggtgaag atccttttg ataatctcat gaccaaaatc ccttaacgtg    3660
agttttcgtt ccactgagcg tcagaccccg tagaaaagat caaaggatct tcttgagatc    3720 cttttttct gcgcgtaatc tgctgcttgc aaacaaaaaa accaccgcta ccagcggtgg    3780
tttgtttgcc ggatcaagag ctaccaactc ttttttccgaa ggtaactggc ttcagcagag    3840
cgcagatacc aaatactgtt cttctagtgt agccgtagtt aggccaccac ttcaagaact    3900
ctgtagcacc gcctacatac ctcgctctgc taatcctgtt accagtggct gctgccagtg    3960
gcgataagtc gtgtcttacc gggttggact caagacgata gttaccggat aaggcgcagc    4020
ggtcgggctg aacggggggt tcgtgcacac agcccagctt ggagcgaacg acctacaccg    4080
aactgagata cctacagcgt gagctatgag aaagcgccac gcttcccgaa gggagaaagg    4140
cggacaggta tccggtaagc ggcagggtcg gaacaggaga gcgcacgagg gagcttccag    4200
ggggaaacgc ctggtatctt tatagtcctg tcgggtttcg ccacctctga cttgagcgtc    4260
gatttttgtg atgctcgtca gggggggcgga gcctatggaa aaacgccagc aacgcggcct    4320
ttttacggtt cctggccttt tgctggcctt ttgctcacat gttctttcct gcgttatccc    4380
ctgattctgt ggataaccgt attaccgcct ttgagtgagc tgataccgct cgccgcagcc    4440
gaacgaccga gcgcagcgag tcagtgagcg aggaagcgga agagcgccca atacgcaaac    4500
cgcctctccc cgcgcgttgg ccgattcatt aatgcagctg gcacgacagg tttcccgact    4560
ggaaagcggg cagtgagcgc aacgcaatta atgtgagtta gctcactcat taggcacccc    4620
aggctttaca ctttatgctt ccggctcgta tgttgtgtgg aattgtgagc ggataacaat    4680
```
ttcacacaag aaggagatat a                                              4701

<210> SEQ ID NO 8
<211> LENGTH: 33
<212> TYPE: DNA
<213> ORGANISM: Artificial Sequence
<220> FEATURE:
<223> OTHER INFORMATION: Chemcially synthesized

<400> SEQUENCE: 8
ctgtcagacc aagtttactc atatatactt tag                                   33

<210> SEQ ID NO 9
<211> LENGTH: 28
<212> TYPE: DNA
<213> ORGANISM: Artificial Sequence
<220> FEATURE:
<223> OTHER INFORMATION: Chemically synthesized

<400> SEQUENCE: 9
actcttcctt tttcaatatt attgaagc                                         28

<210> SEQ ID NO 10
<211> LENGTH: 23
<212> TYPE: DNA
<213> ORGANISM: Artificial Sequence
<220> FEATURE:
<223> OTHER INFORMATION: Chemically synthesized

<400> SEQUENCE: 10
atgagccata ttcaacggga aac                                              23

<210> SEQ ID NO 11
<211> LENGTH: 27
<212> TYPE: DNA
<213> ORGANISM: Artificial Sequence
<220> FEATURE:
<223> OTHER INFORMATION: Chemically synthesized

<400> SEQUENCE: 11
ttagaaaaac tcatcgagca tcaaatg                                          27

<210> SEQ ID NO 12
<211> LENGTH: 31
<212> TYPE: DNA
<213> ORGANISM: Artificial Sequence
<220> FEATURE:
<223> OTHER INFORMATION: Chemically synthesized

<400> SEQUENCE: 12
catatgtata tctccttctt gtgtgaaatt g                                     31

<210> SEQ ID NO 13
<211> LENGTH: 28
<212> TYPE: DNA
<213> ORGANISM: Artificial Sequence
<220> FEATURE:
<223> OTHER INFORMATION: Chemically synthesized

<400> SEQUENCE: 13
cagtggctgc tgccagtggc gataagtc                                         28

<210> SEQ ID NO 14
<211> LENGTH: 36
<212> TYPE: DNA
<213> ORGANISM: Artificial Sequence
<220> FEATURE:

-continued

<223> OTHER INFORMATION: Chemically synthesized

<400> SEQUENCE: 14
catatgaata aatattttga gaacgtatct aaaata                                      36

<210> SEQ ID NO 15
<211> LENGTH: 31
<212> TYPE: DNA
<213> ORGANISM: Artificial Sequence
<220> FEATURE:
<223> OTHER INFORMATION: Chemically synthesized

<400> SEQUENCE: 15
gatatcttaa ggcgcgcctt attctgcaaa c                                           31

<210> SEQ ID NO 16
<211> LENGTH: 75
<212> TYPE: DNA
<213> ORGANISM: Artificial Sequence
<220> FEATURE:
<223> OTHER INFORMATION: Chemically synthesized

<400> SEQUENCE: 16
ttggcgcgcc ttaagatatc aacaaactcc gggaggcagc gtgatgcggc aacaatcaca           60
cggatttccc gtgaa                                                             75

<210> SEQ ID NO 17
<211> LENGTH: 80
<212> TYPE: DNA
<213> ORGANISM: Artificial Sequence
<220> FEATURE:
<223> OTHER INFORMATION: Chemically synthesized

<400> SEQUENCE: 17
catatacctg cacgctgacc acactcactt tccctgaaaa taatccgctc attcagaccg           60
ttcacgggaa atccgtgtga                                                        80

<210> SEQ ID NO 18
<211> LENGTH: 80
<212> TYPE: DNA
<213> ORGANISM: Artificial Sequence
<220> FEATURE:
<223> OTHER INFORMATION: Chemically synthesized

<400> SEQUENCE: 18
ggtcagcgtg caggtatatg ggctatgatg tgcccggcgc ttgaggcttt ctgcctcatg           60
acgtgaaggt ggtttgttgc                                                        80

<210> SEQ ID NO 19
<211> LENGTH: 80
<212> TYPE: DNA
<213> ORGANISM: Artificial Sequence
<220> FEATURE:
<223> OTHER INFORMATION: Chemically synthesized

<400> SEQUENCE: 19
cgtggtggtt aatgaaaatt aacttactac ggggctatct tctttctgcc acacaacacg           60
gcaacaaacc accttcacgt                                                        80

<210> SEQ ID NO 20
<211> LENGTH: 80
<212> TYPE: DNA
<213> ORGANISM: Artificial Sequence
<220> FEATURE:

<223> OTHER INFORMATION: Chemically synthesized

<400> SEQUENCE: 20
aattttcatt aaccaccacg aggcatccct atgtctagtc cacatcagga tagcctctta    60
ccgcgctttg cgcaaggaga                                                80

<210> SEQ ID NO 21
<211> LENGTH: 80
<212> TYPE: DNA
<213> ORGANISM: Artificial Sequence
<220> FEATURE:
<223> OTHER INFORMATION: Chemically synthesized

<400> SEQUENCE: 21
tgagacacac gatcaacaca caccagacaa gggaacttcg tggtagtttc atggccttct    60
tctccttgcg caaagcgcgg                                                80

<210> SEQ ID NO 22
<211> LENGTH: 80
<212> TYPE: DNA
<213> ORGANISM: Artificial Sequence
<220> FEATURE:
<223> OTHER INFORMATION: Chemically synthesized

<400> SEQUENCE: 22
tgtgttgatc gtgtgtctca cactgttgat attcacttat ctgacacgaa aatcgctgtg    60
cgagattcgt tacagagacg                                                80

<210> SEQ ID NO 23
<211> LENGTH: 80
<212> TYPE: DNA
<213> ORGANISM: Artificial Sequence
<220> FEATURE:
<223> OTHER INFORMATION: Chemically synthesized

<400> SEQUENCE: 23
cgcctccagg ttgctactta ccggattcgt aagccatgaa agccgccacc tccctgtgtc    60
cgtctctgta acgaatctcg                                                80

<210> SEQ ID NO 24
<211> LENGTH: 80
<212> TYPE: DNA
<213> ORGANISM: Artificial Sequence
<220> FEATURE:
<223> OTHER INFORMATION: Chemically synthesized

<400> SEQUENCE: 24
taagtagcaa cctggaggcg ggcgcaggcc cgccttttca ggactgatgc tggtctgact    60
actgaagcgc ctttataaag                                                80

<210> SEQ ID NO 25
<211> LENGTH: 73
<212> TYPE: DNA
<213> ORGANISM: Artificial Sequence
<220> FEATURE:
<223> OTHER INFORMATION: Chemically synthesized

<400> SEQUENCE: 25
cggaattcac aacatcagca aggagaaagg ggctaccggc gaaccagcag ccccttata    60 aaggcgcttc agt                                                       73

<210> SEQ ID NO 26

```
<211> LENGTH: 38
<212> TYPE: DNA
<213> ORGANISM: Artificial Sequence
<220> FEATURE:
<223> OTHER INFORMATION: Chemically synthesized

<400> SEQUENCE: 26
tagggctgac atatggctaa aatcgttgtt attggtgc                              38

<210> SEQ ID NO 27
<211> LENGTH: 39
<212> TYPE: DNA
<213> ORGANISM: Artificial Sequence
<220> FEATURE:
<223> OTHER INFORMATION: Chemically synthesized

<400> SEQUENCE: 27
tagggctgaa gatctctaaa ggtttggacg agtaagagc                             39

<210> SEQ ID NO 28
<211> LENGTH: 34
<212> TYPE: DNA
<213> ORGANISM: Artificial Sequence
<220> FEATURE:
<223> OTHER INFORMATION: Chemically synthesized

<400> SEQUENCE: 28
tagggctgac atatggctaa aatcgttgtt attg                                  34

<210> SEQ ID NO 29
<211> LENGTH: 32
<212> TYPE: DNA
<213> ORGANISM: Artificial Sequence
<220> FEATURE:
<223> OTHER INFORMATION: Chemically synthesized

<400> SEQUENCE: 29
tagggctgaa gatctctaaa ggtttggacg ag                                    32

<210> SEQ ID NO 30
<211> LENGTH: 39
<212> TYPE: DNA
<213> ORGANISM: Artificial Sequence
<220> FEATURE:
<223> OTHER INFORMATION: Chemically synthesized

<400> SEQUENCE: 30
gcaggtgcca actggctccc gttttacgat ggaggcaag                             39

<210> SEQ ID NO 31
<211> LENGTH: 24
<212> TYPE: DNA
<213> ORGANISM: Artificial Sequence
<220> FEATURE:
<223> OTHER INFORMATION: Chemically synthesized

<400> SEQUENCE: 31
gagccagttg gcacctgccc aagg                                             24

<210> SEQ ID NO 32
<211> LENGTH: 26
<212> TYPE: DNA
<213> ORGANISM: Artificial Sequence
<220> FEATURE:
<223> OTHER INFORMATION: Chemically synthesized

<400> SEQUENCE: 32
```

-continued catatgaacg ctcccgtccc cgtccc                                          26

<210> SEQ ID NO 33
<211> LENGTH: 26
<212> TYPE: DNA
<213> ORGANISM: Artificial Sequence
<220> FEATURE:
<223> OTHER INFORMATION: Chemically synthesized

<400> SEQUENCE: 33
agatcttcag atggtgaagc gggcac                                          26